United States Patent [19]

Shiveley et al.

[11] Patent Number: 5,856,366
[45] Date of Patent: Jan. 5, 1999

[54] PROCESS FOR MAKING HETEROGENEOUS FOAM MATERIALS

[75] Inventors: Thomas Michael Shiveley, Moscow; Thomas Allen DesMarais; John Collins Dyer, both of Cincinnati; Keith Joseph Stone, Fairfield, all of Ohio

[73] Assignee: The Procter & Gamble Company, Cincinnati, Ohio

[21] Appl. No.: 934,258

[22] Filed: Sep. 19, 1997

Related U.S. Application Data

[62] Division of Ser. No. 612,643, Mar. 8, 1996, Pat. No. 5,817,704.

[51] Int. Cl.$^6$ ........................................................ C08J 9/28
[52] U.S. Cl. .................................. 521/63; 521/64; 521/65
[58] Field of Search .................................. 521/63, 64, 65

[56] References Cited

U.S. PATENT DOCUMENTS

| | | | |
|---|---|---|---|
| 3,255,127 | 6/1966 | Leverkusen et al. | 260/2.5 |
| 3,256,219 | 6/1966 | Will | 260/2.5 |
| 3,431,911 | 3/1969 | Meisel, Jr. | 128/287 |
| 3,565,817 | 2/1971 | Lissant | 252/312 |
| 3,734,867 | 5/1973 | Will | 260/2.5 R |
| 3,763,056 | 10/1973 | Will et al. | 260/2.5 L |
| 4,522,953 | 6/1985 | Barby et al. | 521/64 |
| 4,611,014 | 9/1986 | Jones | 521/146 |
| 4,612,334 | 9/1986 | Jones et al. | 521/146 |
| 4,613,543 | 9/1986 | Dabi | 428/304.4 |
| 4,724,242 | 2/1988 | Vassileff | 521/83 |
| 4,788,225 | 11/1988 | Edwards et al. | 521/147 |
| 4,957,810 | 9/1990 | Eleouet et al. | 428/306.6 |
| 4,966,919 | 10/1990 | Williams, Jr. et al. | 521/54 |
| 4,985,468 | 1/1991 | Elmes et al. | 521/63 |
| 5,021,462 | 6/1991 | Elmes et al. | 521/63 |
| 5,037,859 | 8/1991 | Williams, Jr. et al. | 521/55 |
| 5,149,720 | 9/1992 | DesMarais et al. | 521/63 |
| 5,198,472 | 3/1993 | DesMarais et al. | 521/63 |
| 5,210,104 | 5/1993 | Bass et al. | 521/64 |
| 5,260,345 | 11/1993 | DesMarais et al. | 521/148 |
| 5,268,224 | 12/1993 | DesMarais et al. | 428/286 |
| 5,290,820 | 3/1994 | Brownscombe et al. | 521/64 |
| 5,318,554 | 6/1994 | Young et al. | 604/378 |
| 5,331,015 | 7/1994 | DesMarais et al. | 521/62 |
| 5,336,695 | 8/1994 | Nass et al. | 521/109.1 |
| 5,369,137 | 11/1994 | Paquet et al. | 521/146 |
| 5,387,207 | 2/1995 | Dyer et al. | 604/369 |
| 5,437,823 | 8/1995 | Hetinga et al. | 264/45.5 |
| 5,500,451 | 3/1996 | Goldman et al. | 521/64 |
| 5,550,167 | 8/1996 | DesMarais | 521/50 |
| 5,563,179 | 10/1996 | Stone et al. | 521/64 |
| 5,633,291 | 5/1997 | Dyer et al. | 521/64 |
| 5,646,193 | 7/1997 | Brownscombe et al. | 521/63 |
| 5,650,222 | 7/1997 | DesMarais et al. | 422/370 |

FOREIGN PATENT DOCUMENTS

| | | | |
|---|---|---|---|
| 0 017 671 A1 | 10/1980 | European Pat. Off. | C08J 9/14 |
| 0 017 672 A1 | 10/1980 | European Pat. Off. | C08J 9/00 |
| 0 049 768 A1 | 4/1982 | European Pat. Off. | C08J 9/00 |
| 0 299 762 | 1/1989 | European Pat. Off. | C08F 2/32 |
| 0 561 216 A1 | 9/1993 | European Pat. Off. | B29C 67/22 |
| 0 575 771 A1 | 12/1993 | European Pat. Off. | E04B 1/86 |
| 1340520 | 9/1963 | France . | |
| 1 493 356 | 11/1977 | United Kingdom | C08J 9/28 |
| 2 247 640 | 3/1992 | United Kingdom | B29C 47/06 |
| 2 252 077 | 7/1992 | United Kingdom | B32B 5/32 |
| WO 94/00288 | 1/1994 | WIPO | B29C 67/20 |
| WO 94/28839 | 12/1994 | WIPO | A61F 13/15 |

OTHER PUBLICATIONS

Avar, et al., "Integral Skin Foams and RIM Materials", Polyurethane Handbook, 2nd. ed., G. Oertel Ed., Hanser Publishers, New York, Chapter 7, pp. 329–386 (1993).

Curtain et al., "Polymer Foam Cell Growth in Microgravity", J. Cell. Plas., vol. 28, No. 6, pp. 536–556 (Nov./Dec. 1992).

Lissant, K. J., "The Geometry of High–Internal–Phase Ratio Emulsions", J. of Colloid & Interface Science, vol. 22, No. 5, pp. 462–468 (Nov. 1966).

Lissant et al., "A Study of Medium and High Internal Phase Ratio Water/Polymer Emulsions", J. of Colloid & Interface Science, vol. 42, No. 1, pp. 201–108 (Jan. 1973).

Lissant et al., "Structure of High Internal Phase Ratio Emulsions", J. of Colloid & Interface Science, vol. 47, No. 2, pp. 416–423 (May 1974).

LeMay et al., "Low–Density Microcellular Materials", MRS Bulletin, vol. XV, No. 12, pp. 19–45 (Dec. 1990).

LeMay, J.D., "Mechanical Structure Property Relationships of Microcellular, Low Density Foams", Mat. Res. Soc. Symp. Proc., vol. 207, pp. 21–26, (No Month Identified 1991).

Weber et al., "New Melamine–based Elastic Foam", Kunststoffe, vol. 75, No. 11, pp. 843–848 (Nov. 1985).

(List continued on next page.)

Primary Examiner—Morton Foelak
Attorney, Agent, or Firm—Carl J. Roof; E. Kelly Linman; Jacobus C. Rasser

[57] ABSTRACT

The present invention relates to a HIPE-derived heterogeneous polymeric foam structure of interconnected opencells, wherein the foam structure has at least two distinct regions. Such heterogeneous foams have various applications, such as energy and fluid absorption, insulation, and filtration.

The invention further relates to a heterogeneous absorbent polymeric foam that, upon contact with aqueous fluids (in particular body fluids such as urine and blood), can acquire, distribute, and store these fluids.

The foams of the invention have at least two distinct regions having different density, polymer composition, surface properties, and/or microcellular morphology.

The invention further relates to a process for obtaining the heterogeneous foams by polymerizing a high internal phase water-in-oil emulsion, or HIPE. In one aspect, the process utilizes at least two distinct HIPEs, with each emulsion having a relatively small amount of an oil phase and a relatively greater amount of a water phase.

21 Claims, 13 Drawing Sheet

OTHER PUBLICATIONS

Young et al., "Preparation of multishell ICF target plastic foam cushion materials by thermally induced phase inversion processes", J. Vac. Sci. Technol. vol., 20, No. 4, pp. 1094–1097 (Apr. 1982).

Woods, G., "High Density and Flexible Foams and Microcellular Elastomers", The ICI Polyurethanes Book, Polyurethane and J. Wiley & Sons Publishers, Chpt. 5, pp. 85–100 (1987).

Low Density Cellular Plastics: Physical Basis of Behaviour, Hilyard/Cunningham, Ed., Chapman & Hall, Pub., Fig. 1.3, p. 6 (1994).

Low Density Cellular Plastics: Physical Basis of Behaviour, Hilyard/Cunningham, Ed., Chapman & Hall, Pub., Fig. 3.3, p. 59 (1994).

Handbook of Plastic Foams: Types, Properties, Manufacture and Applications, A. H. Landrock, Ed., Noyes Pub., Fig. 10, p. 57 (1995).

Handbook of Plastic Foams: Types, Properties, Manufacture and Applications, A. H. Landrock, Ed., Noyes Pub., pp. 64–65 (1995). s bg# PROCESS FOR MAKING HETEROGENEOUS FOAM MATERIALS This is a division of application Ser. No. 08/612,643, filed on Mar. 8, 1996 now U.S. Pat. No. 5,817,704.

FIELD OF THE INVENTION

This application relates to flexible, microporous, open-celled polymeric foam materials having two or more distinct regions of different types of foam interspersed so as to deliver a desired mixture of properties in a single piece of material.

BACKGROUND OF THE INVENTION

Flexible open-celled polymeric foams are widely used for energy absorption or insulation (thermal, acoustic, mechanical), filtration, absorption of fluids, and the like. In most cases, the foams desired for these purposes have relatively homogeneous structures comprising cells within a given size range joined by open "windows" or "holes" to adjacent cells. Among the various measures of such foams that are important for each application are cell size/hole size and distribution, anisotropy, proportion of cell struts to windows, and porosity. Anisotropy can arise from the relative deviation between the shape of all the cells in the foam and some geometric ideal. In general, work has been devoted to making foams as homogeneous and isotropic as possible with respect to cell size and shape and density.

Polyurethane foams having a range of densities are known materials. For example, the "integral skin" flexible polyurethane foams have high density skin layers that transition gradually over 1–3 cm into a lower density core region. See for example Ashida, K.; Iwasaki, K. In Handbook of Plastic Foams", Landrock, A. H., ED.; Noyes, 1995; Chapter 2, pp 56, 64–67, incorporated herein by reference. The overall densities of such foams are typically between about 200 and 1,100 kg/m$^3$. These foams do not exhibit distinct regions having different compositional or microstructural properties within a single piece. Typically, these foams also have higher densities, larger cell sizes and/or larger hole sizes than foams which may be preferred for certain applications.

Foams may be made from polymer networks which have been entangled to form an interpenetrating network (IPN). IPNs may exhibit some of the properties of both polymer types. See for example Odian, G. G. "Principles of Polymerization", 3rd edition, Wiley-Interscience: New York, 1991, New York, pp 149–150. IPNs do not inherently relate to control over any features at a supramolecular scale (e.g., density or cell size).

Laminates or sandwiches of two or more layers of foams having differing properties are also well known. See for example, Gibson, L. J.; Ashby, M. F. "Cellular Solids" Pergamon Press: Oxford, 1988, Chapter 9. Formation of such composites requires an additional step and may require use of adhesive which may interfere with the functioning or weight of the foam composite and serves as a potential point of failure.

The development of highly absorbent articles for use as disposable diapers, adult incontinence pads and briefs, and sanitary napkins, is the subject of substantial commercial interest. The ability of such products to acquire, distribute, and store fluids such as are found in body exudates (e.g., urine, sweat, feces, and menses) is obviously critical to their function. Historically, this has been primarily achieved by using a combination of cellulosic fibers and interspersed superabsorbent particles (generally lightly crosslinked partially neutralized polyacrylic acid that forms a gel when exposed to free water). This approach has, however, encountered a number of difficulties in achieving efficient removal of fluid from the body of the wearer and storage away from the wearer, in part due to the difficulty in controlling and maintaining the appropriate blend of particulate and fiber to provide the desired degree of capillary fluid transport and core integrity and flexibility.

Other absorbent materials capable of providing capillary fluid transport include certain types of polymeric foams in absorbent articles for the purpose of imbibing, wicking and/or retaining aqueous body fluids. See, for example, U.S. Pat. No. 3,563,243 (Lindquist), issued Feb. 6, 1971 (absorbent pad for diapers and the like where the primary absorbent is a hydrophilic polyurethane foam sheet); U.S. Pat. No. 4,554,297 (Dabi), issued Nov. 19, 1985 (body fluid absorbing cellular polymers that can be used in diapers or catamenial products); U.S. Pat. No. 4,740,520 (Garvey et al), issued Apr. 26, 1988 (absorbent composite structure such as diapers, feminine care products and the like that contain sponge absorbents made from certain types of super-wicking, crosslinked polyurethane foams). These foams can provide core integrity and flexibility but not the desired degree of capillary fluid transport.

The use of appropriate absorbent foams in absorbent articles such as diapers and catamenial pads can provide features of capillary fluid acquisition, transport and storage required for use in high performance absorbent cores. Absorbent articles containing such foams can possess desirable wet integrity, can provide suitable fit throughout the entire period the article is worn, and can minimize changes in shape during use (e.g., swelling, bunching).

Particularly suitable absorbent low density open-celled foams have been made from High Internal Phase Emulsions (hereafter referred to as "HIPEs"). See, for example, U.S. Pat. No. 5,260,345 (DesMarais et al), issued Nov. 9, 1993; and U.S. Pat. No. 5,268,224 (DesMarais et al), issued Dec. 7, 1993. Other suitable absorbent foams are described in co-pending applications U.S. Ser. No. 08/370,922 (DesMarais et al, filed Jan. 10, 1995); U.S. Ser. No. 08/370,695 (Stone et al., filed Jan. 10, 1995); U.S. Ser. No. 08/370,697 (Dyer, filed Jan. 10, 1995); and U.S. Ser. No. 08/520,793 (DesMarais, filed Aug. 30, 1995), all incorporated by reference herein. The HIPE process provides facile control over the cell and hole size and distribution, proportion of cell struts to windows, and porosity in these foams. When suitably treated to render the surface of these foams hydrophilic, these HIPE foams provide desirable fluid handling properties, including: (a) relatively good wicking and fluid distribution characteristics to transport the imbibed urine or other body fluid away from the initial impingement zone and into the unused balance of the foam structure to allow for subsequent gushes of fluid to be accommodated; and (b) a relatively high storage capacity with a relatively high fluid capacity under load, i.e., under compressive forces. These HIPE absorbent foams are also sufficiently flexible and soft so as to provide a high degree of comfort to the wearer of the absorbent article, and can be made relatively thin until subsequently wetted by the absorbed body fluid.

An important issue associated with the fluid handling properties of an absorbent foam is capillary structure. Foams having larger cell sizes and hole sizes tend to acquire fluid quickly but do not distribute fluid sufficiently against the force of gravity, nor do they store fluid effectively. Conversely, foams having smaller cell sizes and hole sizes are able to wick fluid against the force of gravity and store the fluid tightly to keep it away from the skin of the wearer, but are typically slower to acquire fluid. As indicated, heretofore, these opposing functions in an absorbent article have been achieved primarily by layering, in the z-direction, different types of distinct absorbent foams which provide different functions. This adds complexity and cost to the process and can limit the product designs desired to those which allow for combination of individual pieces. Also, these designs are limited in being able to move fluids by differential capillary pressure only between the layers in the "z-dimension" of the articles, i.e., not in the "x-y dimension" or within the plane of a given layer.

Another important issue is the strength or resistance to compression deflection of the foam. Foams having comparatively higher densities, higher Tgs (defined hereinafter), and/or higher crosslinker levels generally exhibit greater resistance to deforming under pressure. This is achieved at the expense of using more polymer per unit volume, having a foam which deforms too slowly for practical use, or a foam which is too brittle or inflexible.

Accordingly, it would be desirable to be able to make an open-celled polymeric foam material that combines the various properties listed above as distinct regions within one material that: (1) expresses a combination of cell sizes and/or hole sizes in different distinct regions of a single piece of foam, and/or (2) expresses a combination of strengths and flexibilities in a single piece of foam, and/or (3) expresses a combination of energy absorbent properties in a single piece of foam. This can circumvent, at least partially, the need to use separate pieces of foams to serve different purposes, thereby enhancing the efficiency and simplicity of articles made with the objects of the current invention.

SUMMARY OF THE INVENTION

The present invention relates to a HIPE-derived heterogeneous polymeric foam structure of interconnected open-cells, wherein the foam structure has at least two distinct regions. Such heterogeneous foams have various applications, such as energy and fluid absorption, insulation, and filtration.

The invention further relates to a heterogeneous absorbent polymeric foam that, upon contact with aqueous fluids (in particular body fluids such as urine and blood), can acquire, distribute, and store these fluids. Preferably, the heterogenous absorbent polymeric foam of the present invention comprises a hydrophilic, flexible, nonionic polymeric foam structure of interconnected open-cells.

Regardless of whether the heterogeneous foam of the present invention is relatively hydrophobic, or is a hydrophilic foam suitable for aqueous fluid absorption, the foam has at least two distinct regions that differ with regard to one or more of foam density, polymer composition, specific surface area, or microcellular morphology (e.g., cell size, shape, or distribution, or hole size).

The present invention further relates to a process for obtaining the heterogeneous foams by polymerizing a water-in-oil emulsions or HIPE. In one aspect, the process utilizes at least two distinct HIPEs, with each emulsion having a relatively small amount of an oil phase and a relatively greater amount of a water phase. This process comprises the steps of:

A) forming a first water-in-oil emulsion from:
 1) an oil phase comprising:
  a) from about 85 to about 98% by weight of a monomer component capable of forming a copolymer having a Tg of about 95° C. or lower, the monomer component comprising:
   i) from about 20 to about 70% by weight of at least one substantially water-insoluble monofunctional monomer capable of forming an atactic amorphous polymer having a Tg of about 25° C. or lower;
   ii) from about 10 to about 50% by weight of at least one substantially water-insoluble monofunctional comonomer capable of imparting toughness about equivalent to that provided by styrene;
   iii) from about 5 to about 50% by weight of a first substantially water-insoluble, polyfunctional crosslinking agent selected from divinylbenzenes, trivinylbenzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinylsulfone, and mixtures thereof; and
   iv) from 0 to about 15% by weight of a second substantially water-insoluble, polyfunctional crosslinking agent selected from polyfunctional acrylates, methacrylates, acrylamides, methacrylamides, and mixtures thereof; and
  b) from about 2 to about 15% by weight of an emulsifier component which is soluble in the oil phase and which is capable of forming a stable water-in-oil emulsion, the emulsifier component comprising a primary emulsifier having at least about 40% by weight emulsifying components selected from diglycerol monoesters of branched $C_{16}$–$C_{24}$ fatty acids, linear unsaturated $C_{16}$–$C_{22}$ fatty acids, and linear saturated $C_{12}$–$C_{14}$ fatty acids; sorbitan monoesters of branched $C_{16}$–$C_{24}$ fatty acids, linear unsaturated $C_{16}$–$C_{22}$ fatty acids, linear saturated $C_{12}$–$C_{14}$ fatty acids; diglycerol monoaliphatic ethers of branched $C_{16}$–$C_{24}$ alcohols, linear unsaturated $C_{16}$–$C_{22}$ alcohols, and linear saturated $C_{12}$–$C_{14}$ alcohols, and mixtures thereof; and
 2) a water phase comprising an aqueous solution containing: (a) from about 0.2 to about 20% by weight of a water-soluble electrolyte; and (b) an effective amount of a polymerization initiator;
 3) a volume to weight ratio of water phase to oil phase in the range of from about 20:1 to about 200:1;
B) optionally forming a second, distinct water-in-oil emulsion which is different in at least one respect from the first emulsion, but which comprises materials and ranges selected from those listed in parts A)1), A)2), and A)3); and
C) either
 1) a) combining the first and second water-in-oil emulsions in a forming vessel prior to polymerizing the monomer components of either of the water-in-oil emulsions; and
  b) polymerizing both emulsions to form a polymeric, heterogenous foam;
 2) a) partially or completely polymerizing the monomer components in the oil phase of the first water-in-oil emulsion;
  b) combining the material from step C)2)a) and the second water-in-oil emulsion; and c) polymerizing the second emulsion, and the first emulsion if combined when partly cured, to provide a polymeric, heterogeneous foam; or 3) making only the first water-in-oil emulsion while varying the process conditions by which it is formed in a regular fashion using a single emulsion forming head as described hereinafter.

In one embodiment, one of the emulsions generated may be poured into a container or reservoir partially or completely filled with spherical segments or strips of material prepared from a previously polymerized, second emulsion. These spherical segments or strips of material are thoroughly saturated with an aqueous solution closely approximating the composition of the aqueous phase used to form the emulsion added. This mixture is then cured at an appropriate temperature to make a heterogeneous foam of the present invention.

In another embodiment, striped segments of unlike material may be prepared using two or more emulsion forming nozzles expressing different emulsions, layer upon layer, in a forming vessel; or by rhythmically varying the emulsion-making conditions with the single emulsion nozzle. In this case, control over the relative rates of pouring and the relative dispositions of the two nozzles provides control over the spatial relationships of the two (or more) different types of polymeric material developed in the final cured foam.

In a third embodiment, a single emulsion is produced, but one or more of the conditions of shear, water-to-oil ratio, pour temperature, and the like are rhythmically or continuously varied so as to produce regions in the resultant foam of different properties. Thus, unlike the two embodiments described above, formation of the optional second emulsion is not necessary in this embodiment.

In a fourth embodiment, a first unpolymerized emulsion is introduced into a form containing a second emulsion which is not substantially polymerized. By introducing the first emulsion from a nozzle positioned at the bottom of the form while withdrawing the nozzle, the emulsion forms a column or other geometric figure within the second emulsion. The process is repeated. Slices of the cured emulsion thus posses regularly repeating cross sections of the first emulsion in the form of the geometric figure imbedded in the plane of the slice of the second emulsion. Thus, regions of differing properties are introduced within a sheet of material.

In a fifth embodiment, a first emulsion (uncured or cured) is molded or cut to a shape that acts as a mold or fits into a mold for an additional amount of a distinct emulsion, which provides irregular, non-planar cross sections of intimately contacted material in the final cured product.

In a sixth embodiment, a single emulsion is subjected to centrifugation prior to polymerization. Conditions of the centrifugation are mild enough that the water droplets are not ruptured to disrupt the emulsion, but stringent enough to form a density gradient within the emulsion. Upon curing, a density gradient will exist in the foam.

Of course, the skilled artisan will recognize that more than two distinct emulsions can be employed, so as to provide a heterogeneous foam comprising regions with more than two different properties.

DETAILED DESCRIPTION OF THE INVENTION

I. Heterogeneous Polymeric Foam

Figure 1:
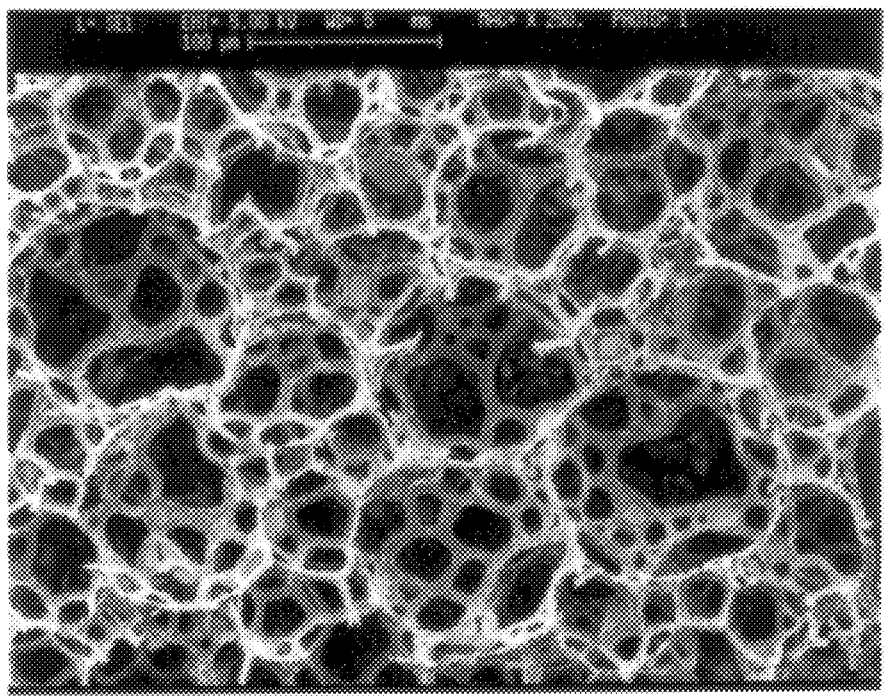
FIG. 1 of the drawings is a photomicrograph (250× magnification) of the first region of a heterogeneous foam having four regions and three interfaces.
Figure 2:
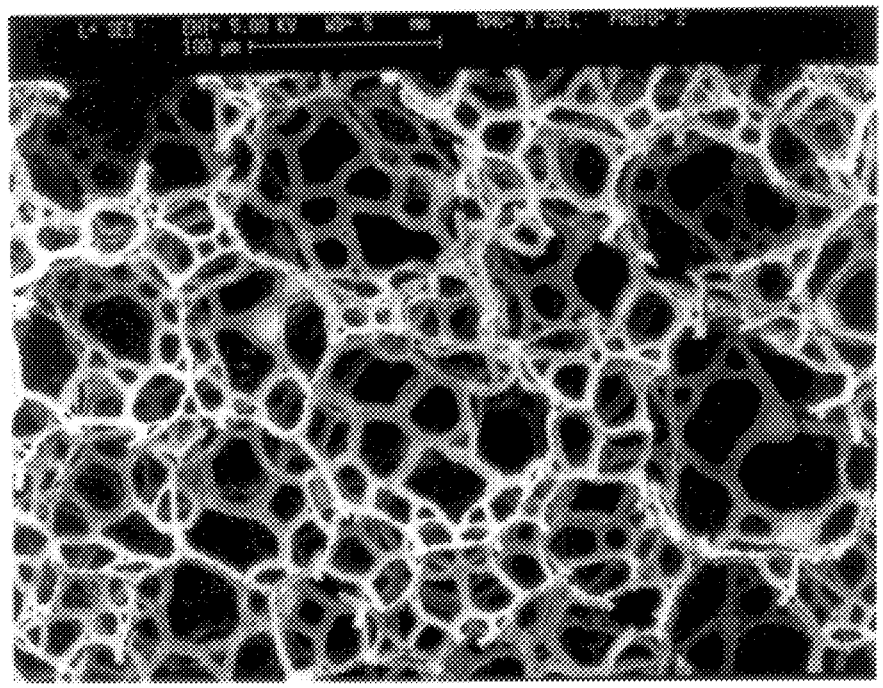
FIG. 2 of the drawings is a photomicrograph (250× magnification) of the second region within the same heterogeneous foam.
Figure 3:
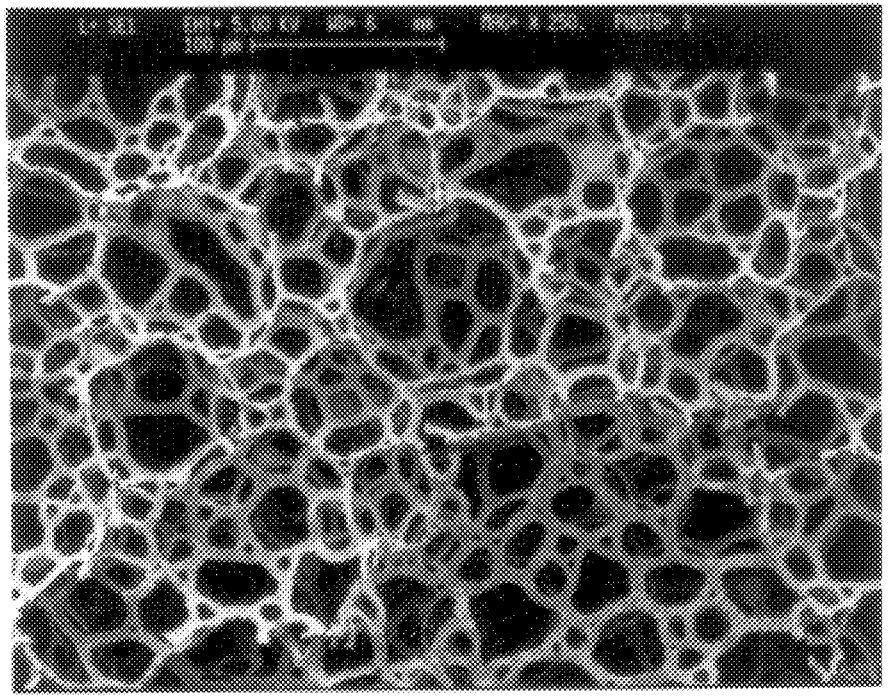
FIG. 3 of the drawings is a photomicrograph (250× magnification) of the second interface of the same heterogeneous foam, where individual pour lines intersect between the second and third regions.
Figure 4:
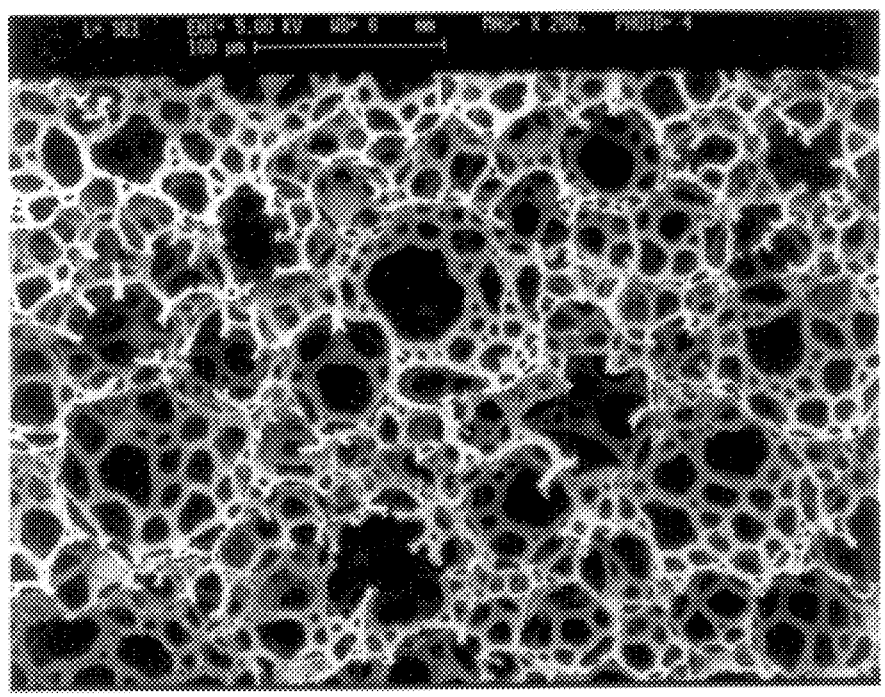
FIG. 4 of the drawings is a photomicrograph (250× magnification) of the third region within the same heterogeneous foam.
Figure 5:
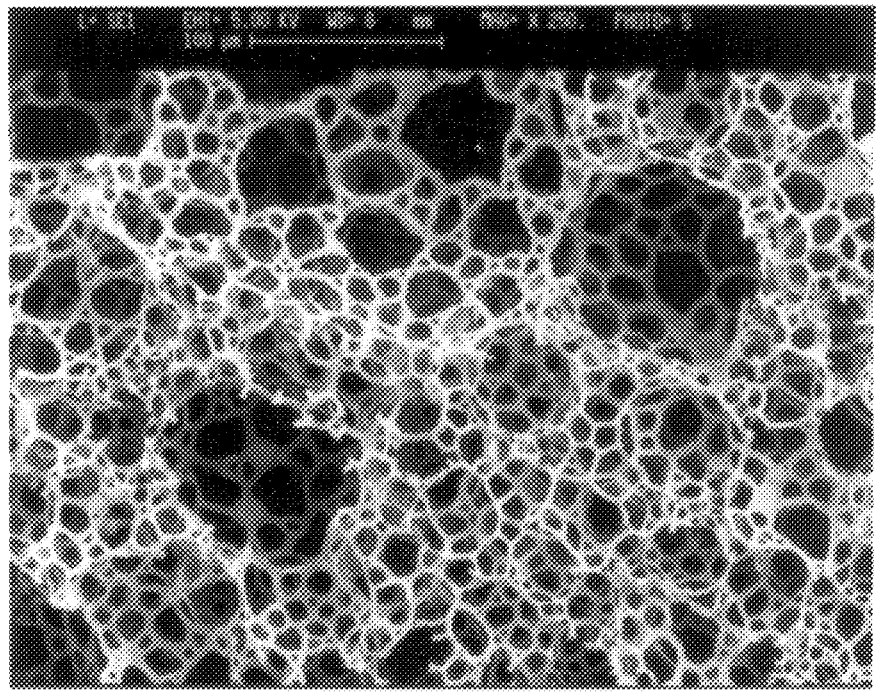
FIG. 5 of the drawings is a photomicrograph (250× magnification) of the third interface of the same heterogeneous, foam where individual pour lines intersect between the third and fourth regions.
Figure 6:
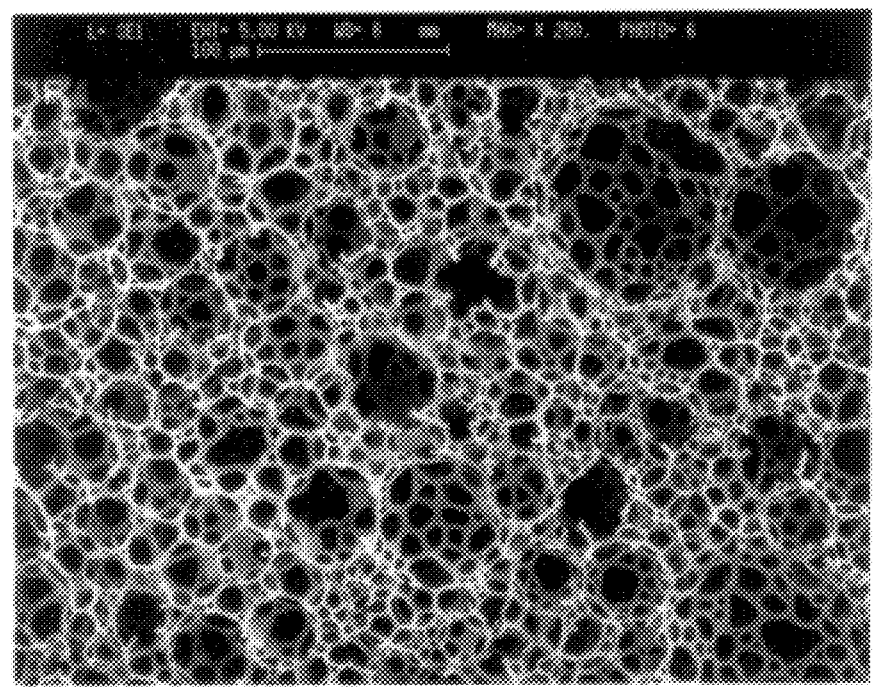
FIG. 6 of the drawings is a photomicrograph (250× magnification) of the fourth region within the same heterogeneous foam.
Figure 7:
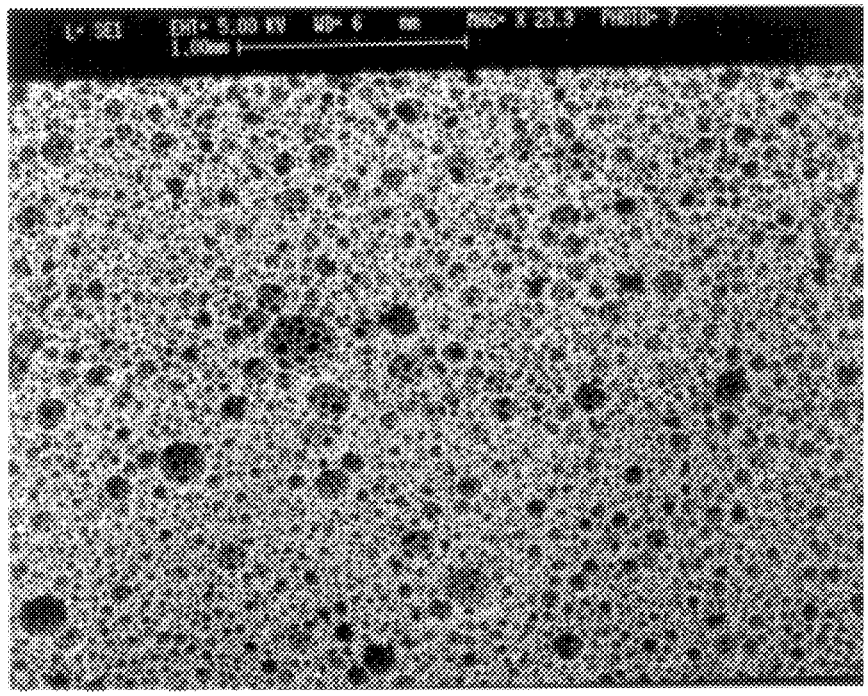
FIG. 7 of the drawings is a photomicrograph (30×) of the first of the three interfaces within the same heterogeneous foam.
Figure 8:
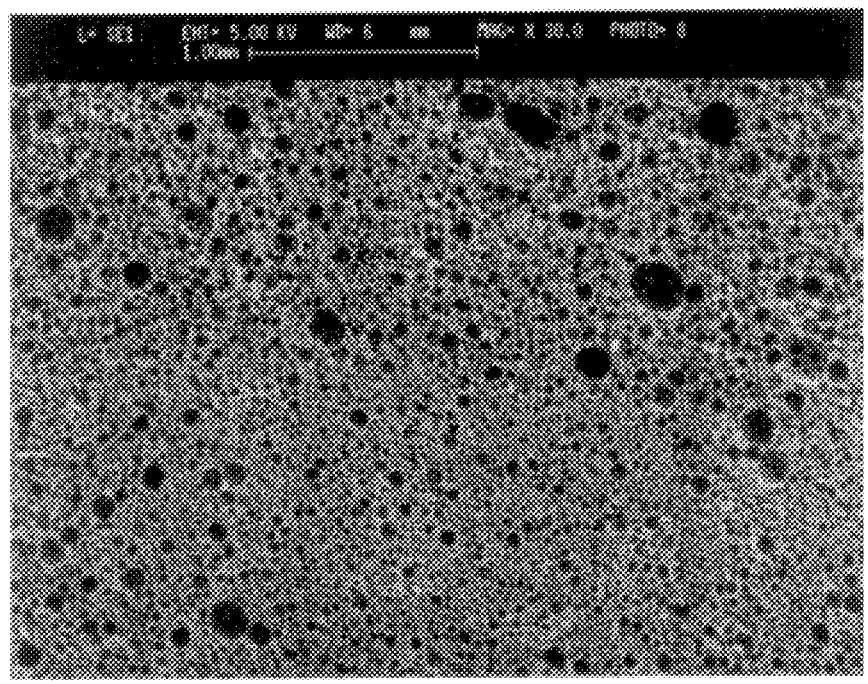
FIG. 8 of the drawings is a photomicrograph (30×) of the second of the three interfaces within the same heterogeneous foams.
Figure 9:
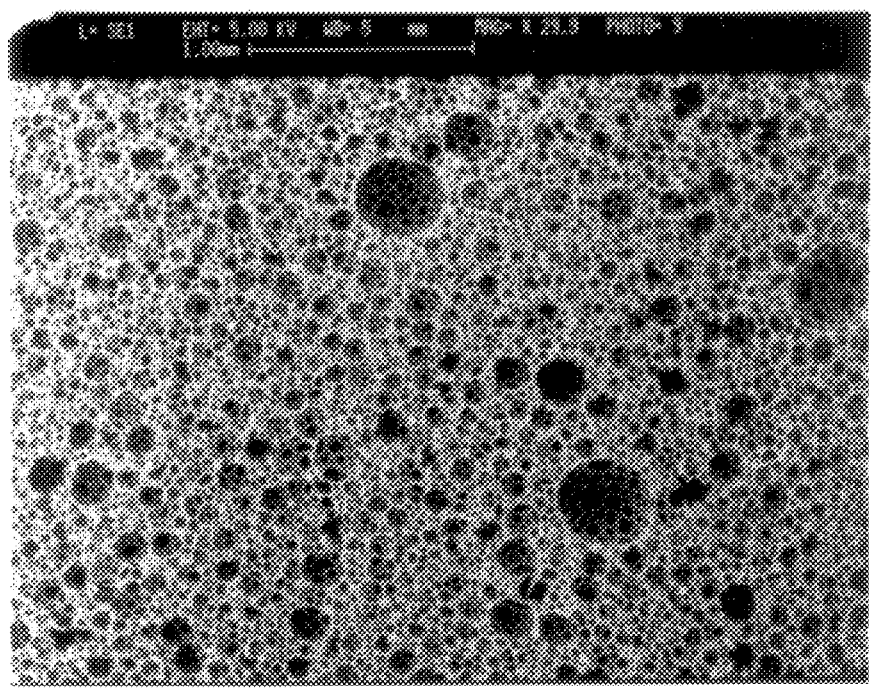
FIG. 9 of the drawings is a photomicrograph (30×) of the third of the three interfaces within the same heterogeneous foams.

The foams of this invention are heterogeneous, open-celled foams. The heterogeneity relates to distinct regions within the same foam which are different in terms of any of the parameters of cell size, hole size, polymer composition, specific surface area or density. The distinct regions are on the macro scale, typically at least millimeter scale dimensions. The foams are preferably of relatively low density having aggregate densities less than about 50 kg/m$^3$ (0.050 g/cc). "Open celled" refers to foams wherein the majority of adjoining cells are in open communication with each other, defined more fully below. These foams are preferably prepared from HIPEs, as described in more detail hereinafter.

The general utility of such heterogeneous foams is broad. For example, foams may be specifically formulated to absorb around a specific frequency of sound energy at a given temperature. Two frequencies may be absorbed by sandwiching two distinct, optimized layers of foam together, requiring an additional process step. The foams of the present invention may be constructed so as to comprise distinct regions optimized to absorb around two or more specific frequencies without the requirement of lamination of two dissimilar pieces of foam.

In filtration applications, the hole size and void volume of the foam governs the efficiency of particulate removal as well as the flow restriction applied to the filtered fluid. A heterogeneous foam of the present invention may be constructed with regions of small holed material interspersed amidst regions of larger holed material so as to filter fine particulates without obstructing the flow of the fluid through the filter. In a recirculating filtration system, the finer particles will eventually be trapped by the smaller holed regions of the heterogeneous foam.

Yet another similar concept applies to absorbent foams wherein a foam of a relatively larger cell size and hole size may more quickly absorb fluid in an absorbent article. Such foams are typically layered over absorbent foams having relatively smaller cell sizes and hole sizes which exert more capillary pressure and drain the acquired fluid from the upper layey, restoring its ability to acquire more fluid. The composite structures well known in the art are limited by the ability to join two separate layers of material, including foam, suitably and conveniently. The foams of the present invention may be so constructed as to provide the properties of two or more separate pieces of foam in one material without any intermediate joining step.

A preferred use of the foams of the present invention is as absorbent core materials in absorbent articles for use as disposable diapers, adult incontinence pads and briefs, and sanitary napkins.

The foam material of the present invention contains at least two regions that differ with regard to their chemical and/or physical make-up. As used herein, the terms "distinct regions" and "distinct foam regions" mean that the regions differ with regard to one or more of foam density, polymer composition, specific surface area, or microcellular morphology (e.g., cell size, hole size). The difference(s) between the discrete regions will be readily measurable. For example, if the difference(s) relates to microstructure, the mean cell diameter or the mean hole diameter in each region should differ by at least about 20%, preferably at least about 35%, more preferably at least about 50%. If the differences relate to density, the densities of the distinct regions should differ by at least about 20%, preferably at least about 35%, more preferably at least about 50%. For example, if one region has a density of 0.020 g/cc, a distinct region should have a density of at least about 0.024 g/cc or less than about 0.016 g/cc, preferably at least about 0.027 g/cc or less than about 0.013 g/cc, and most preferably at least about 0.030 g/cc or less than about 0.010 g/cc. If the differences are compositional in nature, the differences should reflect a relative difference in at least one monomer component of at least about 20%, preferably 35%, more preferably at least about 50%. For example, if one region is composed of about 10% styrene in its formulation, a distinct region should be composed of at least about 12%, preferably at least about 15%, or no more than about 8%, preferably no more than about 5%. Where heterogeneity is based on differences in cell size, if one region contains cells having a mean diameter of about 100 $\mu$m, a distinct region should contain cells having a mean diameter of less than about 80 $\mu$m, preferably less than about 65 $\mu$m, most preferably less than about 50 $\mu$m. Where heterogeneity is based on differences in hole size, if one region contains holes having a mean hole diameter of about 20 $\mu$m, a distinct region should contain cells having a mean hole diameter of less than about 16 $\mu$m, preferably less than about 13 $\mu$m, most preferably less than about 10 $\mu$m. Often, the differences will be as exaggerated as possible, though this will not always be desirable. The differences in regions may comprise all three types of differences discussed above in the ranges indicated. Also, more than two different regions may exist wherein the differences between the three or more distinct regions encompass the same difference ranges discussed above.

Although the foams of the present invention require distinct regions so as to be heterogeneous, these foams may possess a continuum of properties between regions. That is, while in certain embodiments there will be a relatively abrupt change in properties when moving from one region to the next, other embodiments will have a more gradual change of properties between regions.

Where two or more emulsions are employed to provide a heterogeneous foam, the term "distinct emulsions" means that the emulsions will differ to such a degree that their polymerization provides a foam of the present invention, i.e., having the requisite discrete regions. The skilled artisan will recognize what aspects of the emulsions (e.g., monomer reactants, water-to-oil ratio) and/or the conditions for their processing (e.g., shear rates, pour temperature) can be altered to provide foams having the requisite distinct regions. Where a foam is produced using one emulsion, processing conditions will provide the desired differences between regions.

Since the foams of the present invention have, by definition, distinct regions having different properties, the properties of each region may best be measured by using a homogeneous foam prepared in the same way. Some measurement techniques require sample sizes and shapes that are incompatible with the need to distinguish the different properties of each region within the heterogeneous foam. Measurements made on the composite heterogeneous foams in general will reflect by definition a volume or surface area averaged property of the distinct regions unless the measurement is made at a scale smaller than the size of the distinct region itself.

A. General Foam Characteristics

The multi-region foams of the present invention may comprise a dispersed, unconnected region(s) and a continuous region. The dispersed, unconnected region(s) may be in the shape of irregular spherical segments, or larger irregular shapes embedded within a continuous region of dissimilar foam. Alternatively, the distinct regions may be alternating stripes or swirls continuous in only two dimensions. Generally, the foam will consist of a region of discontinuous separated material of like properties dispersed in a region of continuous material having a second set of properties.

The ratio of the volume and/or weight fractions of each region is obviously important, and is readily varied. Preferably, for foams having discontinuous segments, at least about 10% of the foam volume will be the discontinuous segments or the effect may be too small to be beneficial. No more than about 90% of the foam volume will be the discontinuous segments or the effect may dominate the collective properties of the composite foam. Preferably, between about 20% and 50% of the volume of the foam will comprise the discontinuous segment volumes. If the foam is comprised of two or more continuous regions, each having distinct chemical and/or physical properties, preferably between about 20% and 80% of the foam volume will comprise one type with the balance being the other type(s). There is in principle no limit to the number of different regions which may be interspersed to provide a given foam of the present invention.

Figure 16:
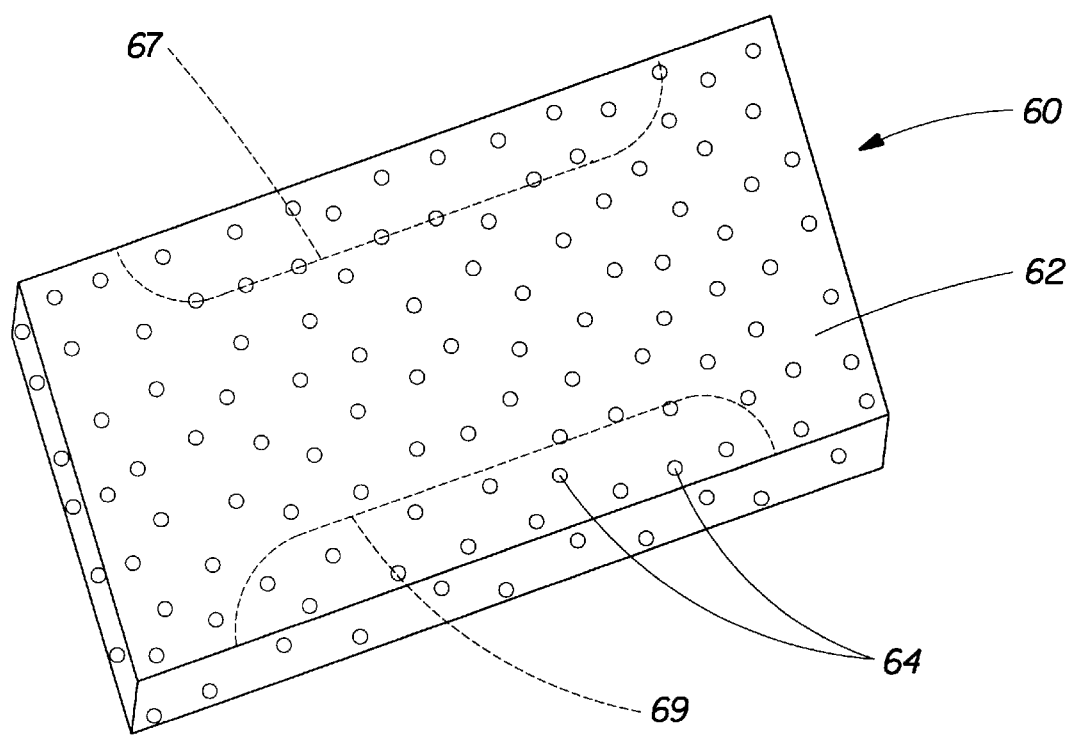
FIG. 16 is a perspective view of a single piece of heterogeneous foam having discontinuous spheres located within a discrete, continuous region.

There are several advantages in using heterogeneous foams. When irregular spherical region(s) are dispersed in a continuous region (as is depicted in FIG. 16), the spherical region(s) may consist of a strong, low density polymer which is resistant to compression but which is too brittle or too high in Tg to use as a continuous sheet. A composite foam consisting of brittle or high Tg region(s) interspersed in a continuous matrix of flexible, tough absorbent polymer will retain the desirable properties of the latter. This composite foam can be made at lower density than a corresponding homogeneous foam. The density of the entire foam will reflect the weighted averages of the densities of the different regions. Such a foam can derive strength from the rigid sections which will have less tendency to collapse under pressure. The continuous flexible section provides the flexibility of the entire foam which would be lacking in a foam consisting only of the rigid polymer. In an alternative embodiment, discrete, unconnected regions may be dispersed in two or more discrete continuous regions.

In addition to modifying the polymer properties of the regions (e.g., Tg, density, brittleness), the microcellular structure can be varied as well. This is particularly useful in combining several types of fluid handling properties in one piece of absorbent foam. For example, a foam having different regions with relatively higher and lower fluid capillary pressure can be developed. This is particularly useful when the regions in the foam piece are continuously dispersed rather than as discontinuous regions. By this method, stripes of material with larger cell sizes and hole sizes are interspersed with stripes of smaller cell sizes and hole sizes. (See FIGS. 13 and 14.) (Of course, other properties, such specific surface area per volume may also or alternatively define the differences between the regions.) The larger cellhole size region will be well suited for fluid acquisition and wicking, and the smaller cell/hole size regions will be better suited for fluid distribution against the force of gravity and storage. These stripes can provide for faster wicking along to a preferred direction in an absorbent article, thereby keeping fluid away from the edges of the article, which is particularly useful in catamenial products. In one embodiment, the heterogeneous foam may comprise one relatively large stripe of large celled, large holed polymer positioned between two smaller stripes of small celled, small holed foam. (See FIG. 13.) This three-region foam may then be C-folded to produce two layers (see FIG. 15), each having a distinct fluid capillary pressure, making the foam suitable for fluid movement within an absorbent article without using a multiplicity of unwind stands for the materials.

Figure 17:
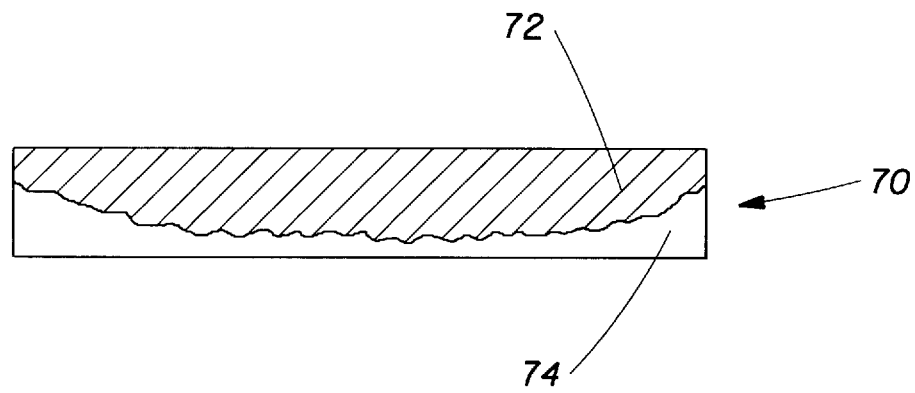
FIG. 17 is a crossectional view of the side of a single piece of heterogeneous foam of the present invention having discrete regions in the z-direction (i.e., thickness) of the foam.
Figure 18:
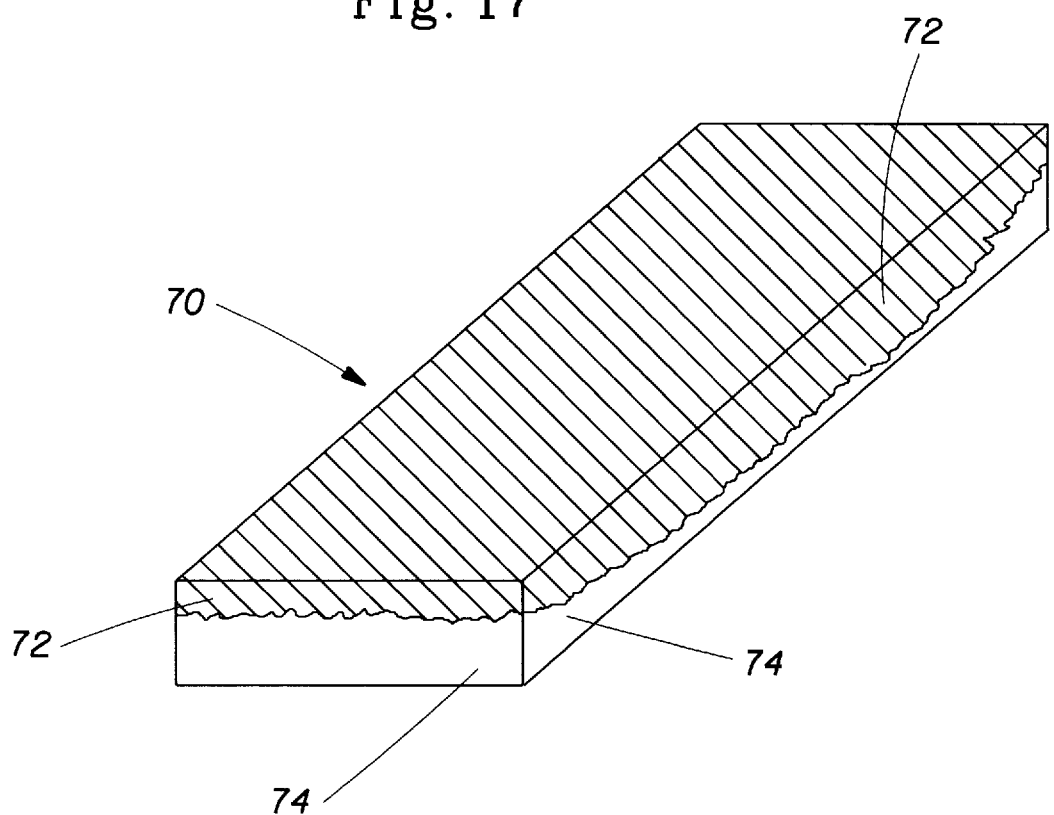
FIG. 18 is a perspective view of the same piece of heterogeneous foam shown in FIG. 17, again showing the discrete regions in the z-direction of the foam.

Alternatively, as depicted in FIGS. 17 and 18, foams of the present invention may be prepared such that the transition from one region to another occurs in the z-direction (i.e., through the thickness) of the foam.

Polymeric foams according to the present invention useful in absorbent articles and structures are those which are relatively open-celled. This means the individual cells of the foam are in complete, unobstructed communication with adjoining cells. The cells in such substantially open-celled foam structures have intercellular openings or "windows" (referred to herein as "holes") that are large enough to permit ready fluid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." For purposes of the present invention, a foam material is "open-celled" if at least 80% of the cells in the foam structure that are at least 1 μm in size are in fluid communication with at least one adjacent cell.

In addition to being open-celled, preferred polymeric foams are sufficiently hydrophilic to permit the foam to absorb aqueous fluids in the amounts specified hereafter. The internal surfaces of the foam structures are rendered hydrophilic by residual hydrophilizing surfactants and/or salts left in the foam structure after polymerization, or by selected post-polymerization foam treatment procedures, as described hereafter.

Preferred hydrophilic, absorbent foams of the present invention will have at least one region particularly suited for acquisition/distribution of body fluids, and at least one region particularly suited for storage of body fluids. Copending U.S. application Ser. No. 08/370,695, filed Jan. 10, 1995 by Stone et al. (Case 5544), and 08/520,793, filed Aug. 30, 1995 by DesMarais (Case 5807), describe foam properties particularly suitable for fluid acquisition/distribution. Copending U.S. application ser. No. 08/563,866, filed Nov. 29, 1995 by DesMarais et al. (Case 5541C) describes foams properties particularly suitable for fluid storage. The disclosures of each of these applications is incorporated by reference herein. The skilled artisan will recognize that the properties described in these copending applications can readily be provided in regions of the foams of the present invention, as desired. Moreover, preferred ranges for the various foam properties described in these copending applications are applicable to the certain of the present hydrophilic foams.

The extent to which the preferred polymeric foams of the present invention are "hydrophilic" can be quantified by the "adhesion tension" value exhibited when in contact with an absorbable test liquid. The adhesion tension exhibited by these foams can be determined experimentally using a procedure where weight uptake of a test liquid, e.g., synthetic urine, is measured for a sample of known dimensions and capillary suction specific surface area. Such a procedure is described in greater detail in the TEST METHODS section of U.S. Pat. No. 5,387,207 (Dyer et al.) issued Feb. 7, 1995, which is incorporated by reference. Foams which are useful as absorbents in the present invention are generally those which exhibit an adhesion tension value of from about 15 to about 65 dynes/cm, more preferably from about 20 to about 65 dynes/cm, as determined by capillary absorption of synthetic urine having a surface tension of 65±5 dynes/cm. After compression, and/or thermal drying/vacuum dewatering to a practicable extent, these polymeric foams may have residual water that includes both the water of hydration associated with the hydroscopic, hydrated salt incorporated therein, as well as free water absorbed within the foam.

For the foams of the present invention to be flexible for their intended use, at least one continuous region of the foam must exhibit an appropriate glass transition temperature (Tg). The Tg represents the midpoint of the transition between the glassy and rubbery states of the polymer. In general, foams that have a higher Tg than the temperature of use can be very strong but will also be very rigid and potentially prone to fracture. Preferably, regions of the foams of the current invention which exhibit either a relatively high Tg or excessive brittleness will be discontinuous. Since these discontinuous regions will also generally exhibit high strength, they can be prepared at lower densities without compromising the overall strength of the composite foam.

Foams intended for applications requiring flexibility should contain at least one continuous region having a Tg as low as possible, so long as the overall foam has acceptable strength at in-use temperatures. Preferably, the Tg of this region will be less than about 30° C. for foams used at about ambient temperature conditions, more preferably less than about 20° C. For foams used in applications wherein the use temperature is higher or lower than ambient, the Tg of the continuous region should be no more that 10° C. greater than the use temperature, preferably the same as use temperature, and most preferably about 10° C. less than use temperature wherein flexibility is desired. Accordingly, monomers are selected as much as possible that provide corresponding homopolymers having lower Tg's. It has been found that the chain length of the alkyl group on the acrylate and methacrylate comonomers can be longer than would be predicted from the Tg of the homologous homopolymer series. Specifically, it has been found that the homologous series of alkyl acrylate or methacrylate homopolymers have a minimum Tg at a chain length of 8 carbon atoms. By contrast, the minimum Tg of the copolymers of the present invention occurs at a chain length of about 12 carbon atoms. (While the alkyl substituted styrene monomers can be used in place of the alkyl acrylates and methacrylates, their availability is currently extremely limited).

A plot of modulus versus temperature for these foams over a temperature range including the glass transition can be revealing. The shape of this curve near the Tg of the polymer of the continuous regions of the foam can show either a sharp or gradual transition as a function of temperature. This shape is particularly relevant where the in-use temperature (usually ambient or body temperature) of the polymer is at or near the Tg. For example, a broader glass-to-rubber transition region can mean an incomplete transition at in-use temperatures. Typically, a broad transition that is incomplete at the in-use temperature indicates that the polymer will evidence greater rigidity and will be less resilient. Conversely, if the transition is sharp and completed at the in-use temperature, then the polymer will exhibit faster recovery from compression when wetted with aqueous fluids. Accordingly, it is desirable to control the Tg and the breadth of the transition region of the polymer to achieve the desired mechanical properties. (The Tg and the width of the transition region are derived from the loss tangent vs. temperature curve from a dynamic mechanical analysis (DMA) measurement, as described in the Test Methods section hereafter).

In one embodiment of the present invention, the polymer of the discontinuous regions of the foam may have Tg's higher than ambient or use temperatures. This efficiently develops resistence to compression deflection to the extent that such segments are incorporated within the continuous matrix of lower Tg material. Generally, the high Tg material will have a Tg from about 30° C. to about 95° C., preferably from about 35° C. to about 75° C., and most preferably between from about 40° C. and about 60° C. For uses not at or near ambient temperature, the Tg of this phase is preferably at least about 10° C. greater than the use temperature. The upper limit is important for the dewatering step described hereinafter. In principal, even higher Tg discontinuous regions may be employed if dewatering is achieved by other techniques (or with pressurized water >100° C.). However, the effect on strength of further increases in the Tg is not realized for applications at room temperature because of the shape of the curve of modulus as a function of temperature which generally has plateaued (in general) by about 50° C. above or below the actual Tg.

B. Capillary Pressures and Forces Within Foam Structure

Certain foams of the present invention have some or all of their regions that will remain in the collapsed state after processing. For such regions the capillary pressures developed at least equal the forces exerted by the elastic recovery or modulus of the compressed polymer in the region. In other words, the capillary pressure necessary to keep the collapsed region relatively thin is determined by the countervailing force exerted by the compressed polymeric foam as it tries to "spring back." The elastic recovery tendency of polymeric foams can be estimated from stress-strain experiments where the expanded foam is compressed to about ⅙ (17%) of its original, expanded thickness and then held in this compressed state until a relaxed stress value is measured. Alternatively, and for the purposes of the present invention, the relaxed stress value is estimated from measurements on the region of the polymeric foam in its collapsed state when in contact with aqueous fluids, e.g., water. This alternative relaxed stress value for a given foam region is hereafter referred to as the "expansion pressure" of the region. The expansion pressure for collapsed polymeric regions of the foams of the present invention is about 30 kiloPascals (kPa) or less and typically from about 7 to about 20 kPa. A detailed description of a procedure for estimating the expansion pressure of foams is set forth in the TEST METHODS section of U.S. Pat. No. 5,387,207 (Dyer et al.) issued Feb. 7, 1995, which is incorporated by reference.

For the purposes of the present invention, it has been found that the specific surface area per foam volume is particularly useful for empirically defining foam structures, or regions thereof, that will remain in a collapsed state. See U.S. Pat. No. 5,387,207 (Dyer et al.) issued Feb. 7, 1995, where specific area per foam volume is discussed in detail. "Specific surface area per foam volume" refers to the capillary suction specific surface area of the foam region times the region's density in the expanded state. This specific surface area per foam volume value is characterized as "empirical" in that it is derived from (a) the capillary suction specific surface area that is measured during wetting of the dried foam structure, and (b) the density of the expanded foam structure after wetting to saturation, rather than by direct measurement of the dried, collapsed foam structure. The tendency of a given polymeric foam or foam region to remain in the collapsed state is a function of its specific surface area per foam volume values and the modulus of the polymeric foam or foam region. Preferably, polymeric foams according to the present invention having one or more regions with a specific surface area per foam volume values of at least about 0.025 $m^2/cc$, preferably at least about 0.05 $m^2/cc$, most preferably at least about 0.07 $m^2/cc$, have been found empirically to remain in a collapsed state with regard to that region (unless the polymer modulus of that foam or region is higher than has typically been found useful in may applications). These regions will be particularly suited for regions that will provide fluid storage. (See U.S. application Ser. No. 08/563,866, discussed above, and U.S. Pat. No. 5,387,207.)

For regions that will provide fluid acquistion/distribution, these regions will preferably have a specific surface area per volume of up to about 0.06 $m^2/cc$, preferably from about 0.0075 to about 0.06 $m^2/cc$, more preferably from about 0.0075 to about 0.04 $m^2/cc$, most preferably from about 0.008 to about 0.02 $m^2/cc$. (See U.S. application Ser. No. 08/520,793, discussed above.)

"Capillary suction specific surface area" is, in general, a measure of the test-liquid-accessible surface area of the polymeric network forming a particular foam per unit mass of the bulk foam material (polymer structural material plus solid residual material). Capillary suction specific surface area is determined both by the dimensions of the cellular units in the foam or its regions, and by the density of the polymer, and is thus a way of quantifying the total amount of solid surface provided by the foam network to the extent that such a surface participates in absorbency.

C. Free Absorbent Capacity

Another important property of certain absorbent foams of the present invention is their free absorbent capacity. "Free absorbent capacity" is the total amount of test fluid (which may be synthetic urine, water, menses, or an organic solvent) which a given foam sample will absorb into its cellular structure per unit mass of solid material in the sample. To be especially useful in absorbent articles for absorbing aqueous fluids, the absorbent foams of the present invention should have an aggregate free absorbent capacity with synthetic urine of from about 20 to about 200 mL, preferably from about 40 to about 120 mL of synthetic urine per gram of dry foam material. The procedure for determining the free absorbent capacity of the foam is described in the TEST METHODS section of U.S. Pat. No. 5,387,207 (Dyer et al.) issued Feb. 7, 1995. While these preferred ranges are capacities for overall foam composites, certain foams of the present invention may comprise distinct regions that may have differing free absorbent capacities resulting from the density differences discussed above. Any measured sample should exhibit the same volume ratio of the distinct regions as a larger piece of the foam to derive a representative measured capacity. Alternatively, the free absorbent capacity may be measured on homogeneous segments of the foams and then a volume average calculation may be used to determine the aggregate value.

D. Resistance to Compression Deflection

An important mechanical feature of the certain polymeric foams of the present invention is their strength in their expanded state, as determined by resistance to compression deflection (RTCD). The RTCD exhibited by the foams herein is a function of the polymer modulus, as well as the density and structure of the foam network. The polymer modulus is, in turn, determined by: a) the polymer composition; b) the conditions under which the foam is polymerized (for example, the completeness of polymerization obtained, specifically with respect to crosslinking); and c) the extent to which the polymer is plasticized by residual material, e.g., emulsifiers, left in the foam structure after processing. RTCD is typically measured on the entire foam (referred to herein as "aggregate RTCD"), even when distinct regions may have distinct values which may be measured separately. A foam which has regions having distinct differences in density and/or polymer modulus will exhibit RTCD properties which are also a function of the geometry of those regions. For example, wherein a striped pattern is formed oriented orthogonally to the load, the load will be resisted by the stronger foam regions (higher density and/or higher modulus) with the weaker foam regions offering little or no effective resistance. A foam wherein the stronger regions are dispersed as particulate segments within a "sea" of weaker more flexible foam will resist compression only in the weaker regions until they have compacted sufficiently for the stronger particulate volume to begin to come into contact and contribute to resistance.

To be useful in many applications (such as absorbent foams in absorbent articles such as diapers), certain foams of the present invention must be suitably resistant to deformation or compression by forces encountered in use when such absorbent materials are engaged in the absorption and retention of fluids. Foams which do not possess sufficient foam strength in terms of RTCD may be able to acquire and store acceptable amounts of body fluid under no-load conditions but will too easily give up such fluid under the compressive stress caused by the motion and activity of the user of the absorbent articles that contain the foam. RTCD is obviously also relevant in uses of these foams in some non-absorbent applications.

The RTCD exhibited by the polymeric foams of the present invention can be quantified by determining the amount of strain produced in a sample of foam held under a certain confining pressure for a specified temperature and period of time. One method for carrying out this particular type of test is described in the TEST METHODS section of U.S. Pat. No. 5,387,207 (Dyer et al.) issued Feb. 7, 1995. Foams useful as absorbents are those which exhibit a RTCD such that a confining pressure of 5.1 kPa (0.74 psi) produces a strain of typically about 80% or less compression of the foam structure when it has been saturated to its free absorbent capacity with synthetic urine having a surface tension of 65±5 dynes/cm. Preferably the strain produced under such conditions will be in the range from about 2 to about 80%, more preferably from about 4 to about 50%, most preferably from about 6 to about 20%. The RTCD of foams of the present invention which are not absorbent or are not intended for use in absorbent products may appropriately be measured in the dry state. One skilled in the art will appreciate that the orientation, geometry and volume fraction of the distinct regions will exert a significant effect on the RTCD values measured due to any anisoptropy induced.

E. Other Properties of Polymeric Foam

Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Similarly, the diameter of the holes connecting the cells is used in characterizing such foams. Since cells and holes between cells in a given sample of polymeric foam will not necessarily be of approximately the same size, a mean cell size, i.e., mean cell diameter, and/or a mean hole size, will often be specified. For foams of the present invention, each region may possess a different mean cell size and/or a different hole size. Each region may also possess a different distribution about that mean, e.g., one region may contain cells of mean diameter of 130 $\mu$m (or a mean hole diameter of about 26 $\mu$m) with 90% of all defineable cells being between about 80 $\mu$m and 180 $\mu$m (and holes between about 16 and 36 $\mu$m), while the distinct region may contain cells of mean diameter of 50 $\mu$m (or a mean hole diameter of about 10 $\mu$m) with 90% of all defineable cells being between about 20 $\mu$m and 80 $\mu$m (and holes between about 16 and 36 $\mu$m). The distribution curves of the two regions may overlap though the means will be quite distinct.

A number of techniques are available for determining the average cell size and average hole size of foams. The most useful technique, however, for determining cell size and hole size in foams involves a simple measurement based on the scanning electron photomicrograph of a foam sample. FIG. 1, for example, shows a typical HIPE foam structure according to the present invention in its expanded state. Superimposed on the photomicrograph is a scale representing a dimension of 100 $\mu$m. Such a scale can be used to determine average cell size via an image analysis procedure, or by simple visual approximation and averaging.

The cell and hole size measurements given herein are based on the number average cell size and number average hole size of the foam in its expanded state, e.g., as shown in FIG. 1.

Preferred foams of the present invention will have one or more regions suitable for acquisition of fluid having a mean cell diameter of from about 20 to about 200 $\mu$m, preferably from about 50 to about 190 $\mu$m, and most preferably from about 80 to about 180 $\mu$m; and a mean hole size of from about 5 to about 45 $\mu$m, preferably from about 8 to about 40 $\mu$m, and most preferably from about 20 to about 35 $\mu$m. These foams will also preferably have one or more fluid storage regions having a mean cell diameter of not more than about 50 $\mu$m, preferably from about 5 to about 35 $\mu$m; and a mean hole size not more than about 10 $\mu$m, preferably from about 1 to about 7 $\mu$m.

"Foam density" (i.e., in grams of foam per cubic centimeter of foam volume in air) is specified herein on a dry basis. Foam density of the present foams is typically measured on the entire foam even when distinct regions may have distinct values which may be measured separately. The aggregate density of a foam having two or more distinct regions of polymer with different densities would simply be the volume averaged densities from each area. Typically, the aggregate density will range between about 0.04 g/cc and 0.01 g/cc, while the densities of the distinct regions may vary more widely. Specifically, regions wherein very hard but low density segments are present will typically be between about 0.02 and 0.005 g/cc. Regions of more flexible foam will typically be between about 0.05 and 0.02 g/cc. As an example, a foam of the present invention might comprise 30% of its volume as a brittle strong foam having a density of 0.01 g/cc and 70% of its volume a flexible foam having a density of 0.03 g/cc. The calculated aggregate density of this foam would be about 0.024 g/cc.

The procedure for measuring aggregate foam density is described in U.S. Pat. No. 5,387,207 (Dyer et al.) issued Feb. 7, 1995. The amount of absorbed water-soluble residual materials, e.g., residual salts and liquid left in the foam, for example, after HIPE polymerization, washing and/or hydrophilization, is disregarded in calculating and expressing foam density. Foam density does include, however, other water-insoluble residual materials such as emulsifiers present in the polymerized foam. Such residual materials can contribute significant mass to the foam material.

Preferred absorbent foams will in general exhibit especially desirable and useful aqueous fluid handling and absorbency characteristics. The fluid handling and absorbency characteristics that are most relevant for absorbent foams and regions thereof are: A) the rate of vertical wicking of fluid through the foam structure or regions of the foam structure; B) the absorbent capacity of the foam or regions thereof at specific reference wicking heights; C) the ability of one region of the absorbent foam structures to drain (partition) fluid from another region and D) the ability of the absorbent foam structures to drain (partition) fluid from competing absorbent structures with which the foam can be in contact.

Vertical wicking, i.e., fluid wicking in a direction opposite from gravitational force, is an especially desirable performance attribute for absorbent foams herein. These foams will frequently be utilized in absorbent articles in a manner such that fluid to be absorbed must be moved within the article from a relatively lower position to a relatively higher position within the absorbent core of the article. Since rapid wicking tends to be contrary with having high fluid capillary pressure, foams with distinct regions having each property maximized can be preferred. Accordingly, the ability of specific regions within these foams to wick fluid rapidly against gravitational forces is particularly relevant to their functioning as absorbent components in absorbent articles.

Vertical wicking is determined by measuring the time taken for a colored test liquid (e.g., synthetic urine) in a reservoir to wick a vertical distance of 5 cm through a test strip of foam of specified size. The vertical wicking procedure is described in greater detail in the TEST METHODS section of U.S. Pat. No. 5,387,207 (Dyer et al.) issued Feb. 7, 1995, (herein incorporated by reference), but is performed at 31° C., instead of 37° C. To be especially useful in absorbent articles for absorbing urine, at least certain of the distinct regions of the foam absorbents of the present invention will preferably wick synthetic urine (65±5 dynes/cm) to a height of 5 cm in no more than about 30 minutes. More preferably, the distinct regions of the preferred foam absorbents of the present invention wick synthetic urine to a height of 5 cm in no more than about 5 minutes.

The vertical wicking absorbent capacity test measures the amount of test fluid per gram of absorbent foam that is held within each one inch (2.54 cm) vertical section of the same standard size foam sample used in the vertical wicking test. Such a determination is generally made after the sample has been allowed to vertically wick test fluid to equilibrium (e.g., after about 18 hours). Like the vertical wicking test, the vertical wicking absorbent capacity test is described in greater detail in the TEST METHODS section of U.S. Pat. No. 5,387,207 (Dyer et al.) issued Feb. 7, 1995, which is incorporated by reference.

Another important property of useful absorbent foams according to the present invention is their capillary absorption pressure. Capillary absorption pressure refers to the ability of the foam to wick fluid vertically. [See P. K. Chatterjee and H. V. Nguyen in "Absorbency," Textile Science and Technology, Vol. 7; P. K. Chatterjee, Ed.; Elsevier: Amsterdam, 1985; Chapter 2.] For the purposes of the present invention, the capillary absorption pressure of interest is the hydrostatic head at which the vertically wicked fluid loading is 50% of the free absorbent capacity under equilibrium conditions at 31° C. The hydrostatic head is represented by a column of fluid (e.g., synthetic urine) of height h.

Figure 13:
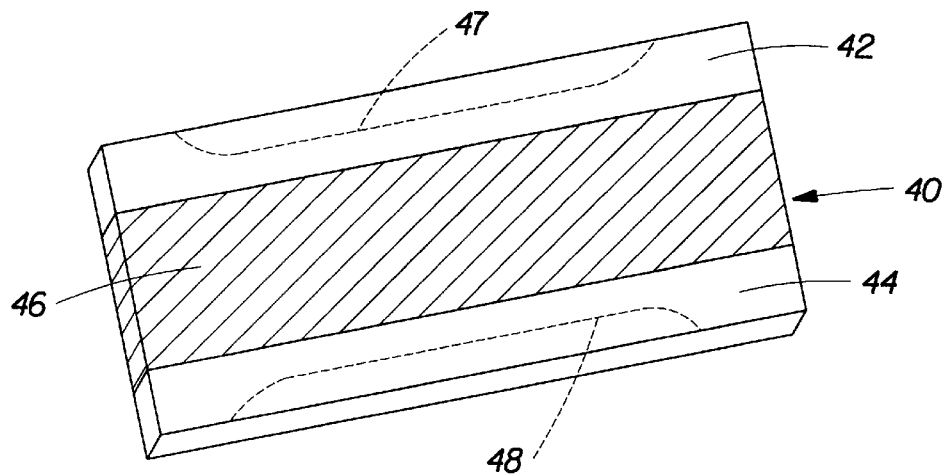
FIG. 13 of the drawings is a perspective view of a single piece of heterogeneous foam of the present invention having three distinct regions, where the middle region is a relatively large celled structure and the two outer regions are both relatively small celled structures. Alternatively, the distinct regions may differ with regard to capillary suction specific surface area per volume.

To be especially useful in absorbent articles for absorbing aqueous fluids, at least certain regions of the preferred absorbent foams of the present invention will generally have a capillary absorption pressure of at least about 10 cm. (Foams of the present invention typically have absorption pressures of from about 18 to about 45 cm.) Since it is not convenient experimentally to measure an aggregate capillary absorption pressure with the heterogeneous foams of this invention wherein the heterogeneity relates to cell size or surface area or hydrophilicity, these properties are measured on homogeneous foams prepared identically to the distinct regions of the heterogeneous foams. It may be highly desirable, for example, to have a foam as illustrated by FIG. 13 where the outside regions (42 and 44) comprise distinct regions wherein capillary absorption pressure is 30 cm and the center region (46) has a capillary absorption pressure of about 10 cm. This provides a structure capable of rapid acquisition in the center area and subsequent fluid movement from that area by capillary action to the outer areas.

II. Preparation of Polymeric Foams From HIPEs Having Relatively High Water-to-Oil Ratios A. In General Polymeric foams according to the present invention can be prepared by polymerization of certain water-in-oil emulsions having a relatively high ratio of water phase to oil phase commonly known in the art as "HIPEs." Polymeric foam materials which result from the polymerization of such emulsions are referred to hereafter as "HIPE foams." The disclosure concerning the starting materials, processing conditions, etc. for preparation of the foams of the present invention may refer to one emulsion. However, it is understood that the foams of the present invention may be formed from at least two such HIPEs, so long as the HIPEs differ sufficiently to provide the distinct regions of the present foams. Where two or more distinct emulsions are used, each emulsion will comprise materials described below, in the ranges indicated, but will obviously differ so as to be distinct.

The relative amounts of the water and oil phases used to form the HIPE(s) are, among many other parameters, important in determining the structural, mechanical and performance properties of the resulting polymeric foams. In particular, the ratio of water to oil in the respective emulsion (s) can influence the density, cell size, and capillary suction specific surface area of the corresponding regions of the foam and dimensions of the struts that form the foam's regions. The emulsion(s) used to prepare the heterogeneous HIPE foams of the present invention will generally have a volume to weight ratio of water phase to oil phase in the range of from about 20:1 to about 150:1, more preferably from about 30:1 to about 75:1, most preferably from about 40:1 to about 65:1. The general preparation of HIPE foams is described in detail in U.S. Patent 5,387,207 (Dyer et al.) issued Feb. 7, 1995.

1. Oil Phase Components

The continuous oil phase of the HIPE(s) comprises monomers that are polymerized to form the solid foam structure. This monomer component is formulated to be capable of forming a copolymer having a Tg of about 35° C. or lower or about 95° C. or lower, depending on which distinct phase is to be formed in those embodiments where regions having different Tgs is desired. Where such differences are desired, typically, the low Tg region will have a Tg from about 0° to about 30° C. and the high Tg region will have a Tg from about 35° to about 95° C. (The method for determining Tg by Dynamic Mechanical Analysis (DMA) is described hereafter in the TEST METHODS section.) The monomer component includes: (a) at least one monofunctional monomer whose atactic amorphous polymer has a Tg of about 25° C. or lower (see Brandup, J.; Immergut, E. H. "Polymer Handbook", 2nd Ed., Wiley-Interscience, New York, N.Y., 1975, III–139.); (b) at least one monofunctional comonomer to improve the toughness or tear resistance of the foam; (c) a first polyfunctional crosslinking agent; and (d) optionally a second polyfunctional crosslinking agent. Selection of particular types and amounts of monofunctional monomer (s) and comonomer(s) and polyfunctional cross-linking agent(s) can be important to the realization of HIPE foams having the desired combination of structure, mechanical, and fluid handling (where absorbent foams are desired) properties which render such materials suitable for use in the invention herein.

The monomer component comprises one or more monomers that tend to impart rubber-like properties to the resulting polymeric foam structure. Such monomers can produce high molecular weight (greater than 10,000) atactic amorphous polymers having Tgs of about 25° C. or lower. Monomers of this type include, for example, the ($C_4$–$C_{14}$) alkyl acrylates such as butyl acrylate, hexyl acrylate, octyl acrylate, 2-ethylhexyl acrylate, nonyl acrylate, decyl acrylate, dodecyl (lauryl) acrylate, isodecyl acrylate, tetradecyl acrylate; aryl and alkaryl acrylates such as benzyl acrylate and nonylphenyl acrylate; the ($C_6$–$C_{16}$) alkyl methacrylates such as hexyl methacrylate, octyl methacrylate, nonyl methacrylate, decyl methacrylate, isodecyl methacrylate, dodecyl (lauryl) methacrylate, tetradecyl methacrylate, acrylamides such as N-octadecyl acrylamide, ($C_4$–$C_{12}$) alkyl styrenes such as p-n-octylstyrene, isoprene, butadiene, 1,3-pentadiene, 1,3,7-octatriene, β-myrcene, and combinations of such monomers. Of these monomers, isodecyl acrylate, dodecyl acrylate and 2-ethylhexyl acrylate are the most preferred. The monofunctional monomer(s) will generally comprise 20 to about 70%, more preferably from about 40 to about 65%, by weight of the monomer component.

The monomer component utilized in the oil phase of the HIPE(s) also comprises one or more monofunctional comonomers capable of imparting toughness about equivalent to that provided by styrene to the resulting region of the polymeric foam structure. Tougher foam regions exhibit the ability to deform substantially without failure. These monofunctional comonomer types can include styrene-based comonomers (e.g., styrene and ethyl styrene) or other monomer types such as methyl methacrylate where the related homopolymer is well known as exemplifying toughness. The preferred monofunctional comonomer of this type is a styrene-based monomer with styrene and ethyl styrene being the most preferred monomers of this kind. The monofunctional "toughening" comonomer will normally comprise from about 10 to about 50%, preferably from about 15% to about 30%, most preferably from about 18% to about 22%, by weight of the monomer component.

In certain cases, the "toughening" comonomer can also impart the desired rubber-like properties to the resultant polymer. The $C_4$–$C_{12}$ alkyl styrenes, and in particular p-n-octylstyrene, are examples of such comonomers. For such comonomers, the amount that can be included in the monomer component will be that of the typical monomer and comonomer combined.

The monomer component also contains a first (and optionally second) polyfunctional crosslinking agent. As with the monofunctional monomers and comonomers, selection of the particular type and amount of crosslinking agents is very important to the eventual realization of preferred polymeric foams having the desired combination of structural, mechanical, and fluid-handling properties.

The first polyfunctional crosslinking agent can be selected from a wide variety of monomers containing two or more activated vinyl groups, such as divinylbenzenes, trivinyl benzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinyifurans, divinylsulfide, divinylsulfone, and mixtures thereof. Divinylbenzene is typically available as a mixture with ethyl styrene in proportions of about 55:45. These proportions can be modified so as to enrich the oil phase with one or the other component. Generally, it is advantageous to enrich the mixture with the ethyl styrene component while simultaneously reducing the amount of styrene in the monomer blend. The preferred ratio of divinylbenzene to ethyl styrene is from about 30:70 to 55:45, most preferably from about 35:65 to about 45:55. The inclusion of higher levels of ethyl styrene imparts the required toughness without increasing the Tg of the resulting copolymer to the degree that styrene does. This first cross-linking agent can generally be included in the oil phase of the HIPE in an amount of from about 5 to about 50%, more preferably from about 12 to about 35%, most preferably from about 12% to about 25%, by weight of the monomer component (calculated on a 100% basis for the active portion of the crosslinker if a blend).

The optional second crosslinking agent can be selected from polyfunctional acrylates, methacrylates, acrylamides, methacrylamides, and mixtures thereof. These include di-, tri-, and tetra-acrylates, as well as di-, tri-, and tetra-methacrylates, di-, tri-, and tetra-acrylamides, as well as di-, tri-, and tetra-methacrylamides; and mixtures of these crosslinking agents. Suitable acrylate and methacrylate crosslinking agents can be derived from diols, triols and tetraols that include 1,10-decanediol, 1,8-octanediol, 1,6-hexanediol, 1,4-butanediol, 1,3-butanediol, 1,4-but-2-enediol, ethylene glycol, diethylene glycol, trimethylolpropane, pentaerythritol, hydroquinone, catechol, resorcinol, triethylene glycol, polyethylene glycol, sorbitol and the like. (The acrylamide and methacrylamide crosslinking agents can be derived from the equivalent diamines, triamines and tetramines). The preferred diols have at least 2, more preferably at least 4, most preferably 6, carbon atoms. This second cross-linking agent can generally be included in the oil phase of the HIPE in an amount of from 0 to about 15%, preferably from about 7to about 13%, by weight of the monomer component.

Without being bound by theory, it is believed this second crosslinking agent generates a more homogeneously crosslinked structure that develops strength more efficiently than using either the first or the second crosslinker alone at comparable levels. The second crosslinker also has the effect of broadening the glass-to-rubber transition region. This broader transition can be tailored to meet specific strength, resilience, and/or energy absorption requirements at in-use temperatures by controlling the relative amount of the two crosslinker types employed. Thus, a foam containing only the first type of crosslinker will exhibit a relatively sharp transition that can be useful if higher resilience is desired and if the Tg is very close to the final in-use temperature. This is particularly useful in sound absorption applications wherein the foam will absorb sound or mechanical vibrational energy around an optimum frequency at a given temperature depending on the shape and maximum in this transition. Increasing the amount of the second crosslinker serves to broaden the transition, even if the actual transition temperature itself has not changed.

The major portion of the oil phase of the HIPEs will comprise the aforementioned monomers, comonomers and crosslinking agents. It is essential that these monomers, comonomers and crosslinking agents be substantially water-insoluble so that they are primarily soluble in the oil phase and not the water phase. Use of such substantially water-insoluble monomers ensures that HIPEs of appropriate characteristics and stability will be realized. It is, of course, highly preferred that the monomers, comonomers and crosslinking agents used herein be of the type such that the resulting heterogeneous polymeric foam is suitably non-toxic and appropriately chemically stable. These monomers, comonomers and cross-linking agents should preferably have little or no toxicity if present at very low residual concentrations during post-polymerization foam processing and/or use.

Another essential component of the oil phase of the HIPEs is an emulsifier component that comprises at least a primary emulsifier. Suitable primary emulsifiers have been found to be those which: (1) are soluble in the oil phase of the HIPE; (2) provide a minimum oil phase/water phase interfacial tension (IFT) of from about 0.06 to about 5 dyne/cm, preferably from about 0.1 to about 3 dyne/cm; (3) provide a critical aggregate concentration (CAC) of about 5 wt. % or less, preferably about 3 wt. % or less; (4) form HIPEs that are sufficiently stable against coalescence at the relevant drop sizes and the relevant process conditions (e.g., HIPE formation and polymerization temperatures); and (5) desirably have a high concentration of "interfacially active" component(s) capable of lowering the interfacial tension between the oil and water phases of the HIPE. While not being bound by theory, it is believed that the concentration of interfacially active components needs to be sufficiently high to provide at least approximately monolayer coverage to internal oil phase droplets at the preferred drop sizes, water:oil ratios, and emulsifier levels. Typically, these primary emulsifiers: (6) have melt and/or solid-to-liquid crystalline phase-transition temperatures of about 30° C. or less; (7) are water dispersible; (8) are substantially water insoluble or at least do not appreciably partition into the water phase under the conditions of use. It is preferred that the primary emulsifier provide sufficient wettability when spread on a hydrophobic surface (e.g., the polymeric foam) such that the advancing contact angle for synthetic urine is less than (preferably substantially less than) 90°. (The method of measurement for IFT. and CAC is described in the TEST METHODS section hereafter.) These primary emulsifiers also preferably hydrophilize the resulting polymeric foam. These primary emulsifiers typically comprise at least about 40%, preferably at least about 50%, more preferably at least about 70%, emulsifying components selected from diglycerol monoesters of branched $C_{16}$–$C_{24}$ fatty acids, linear unsaturated $C_{16}$–$C_{22}$ fatty acids, or linear saturated $C_{12}$–$C_{14}$ fatty acids, such as diglycerol monooleate (i.e., diglycerol monoesters of C18:1 fatty acids), diglycerol monomyristate, diglycerol monoisostearate, and diglycerol monoesters of coconut fatty acids; sorbitan monoesters of branched $C_{16}$–$C_{24}$ fatty acids, linear unsaturated $C_{16}$–$C_{22}$ fatty acids, and linear saturated $C_{12}$–$C_{14}$ fatty acids, such as sorbitan monooleate, sorbitan monomyristate, and sorbitan monoesters derived from coconut fatty acids; diglycerol monoaliphatic ethers of branched $C_{16}$–$C_{24}$ alcohols, linear unsaturated $C_{16}$–$C_{22}$ alcohols, and linear saturated $C_{12}$–$C_{14}$ alcohols, and mixtures of these emulsifying components. The preferred primary emulsifiers are diglycerol monooleate (e.g., preferably greater than about 40%, more preferably greater than about 50%, most preferably greater than about 70% diglycerol monooleate), sorbitan monooleate (e.g., preferably greater than about 40%, more preferably greater than about 50%, most preferably greater than about 70% sorbitan monooleate), and diglycerol monoisostearate (e.g., preferably greater than about 40%, more preferably greater than about 50%, most preferably greater than about 70% diglycerol monoisostearate).

Diglycerol monoesters of linear saturated, linear unsaturated and branched fatty acids useful as emulsifiers in the present invention can be prepared by esterifying diglycerol with fatty acids, using procedures well known in the art. See, for example, the method for preparing polyglycerol esters disclosed in U.S. Pat. No. 5,387,207 (Dyer et al.) issued Feb. 7, 1995, which is incorporated by reference. Diglycerol can be obtained commercially or can be separated from polyglycerols that are high in diglycerol. Linear saturated, linear unsaturated and branched fatty acids can be obtained commercially. The mixed ester product of the esterification reaction can be fractionally distilled under vacuum one or more times to yield distillation fractions that are high in diglycerol monoesters.

Linear saturated, linear unsaturated or, branched diglycerol monoaliphatic ethers can also be prepared and their composition determined using procedures well known in the art. See also U.S. Pat. No. No. 5,500,451 issued Mar. 19, 1996 by Goldman et al, which is incorporated by reference.

Sorbitan esters of linear, branched, and unsaturated fatty acids can be obtained commercially or prepared using methods known in the art. See, for example, U.S. Pat. No. 4,103,047 (Zaki et al), issued Jul. 25, 1978 (herein incorporated by reference), especially column 4, line 32 to column 5, line 13. The mixed sorbitan ester product can be fractionally vacuum distilled to yield compositions that are high in sorbitan monoesters. Sorbitan ester compositions can be determined by methods well known in the art such as small molecule gel permeation chromatography. See copending U.S. application Ser. No. 08/514,346, which describes the use of this method for polyglycerol monoaliphatic ethers.

In addition to these primary emulsifiers, secondary emulsifiers can be optionally included in the emulsifier component. These secondary emulsifiers are at least cosoluble with the primary emulsifier in the oil phase and can be included to: (1) increase the stability of the HIPE against coalescence of the dispersed water droplets, especially at higher water-to-oil ratios and higher HIPE formation and polymerization temperatures, (2) modify the minimum IFT between oil and water phases to within the range of from about 0.06 to about 5 dyne/cm, (3) lower the CAC of the emulsifier component, or (4) increase the concentration of interfacially active components. Suitable secondary emulsifiers can be zwitterionic types, including the phosphatidyl cholines and phosphatidyl choline-containing compositions such as the lecithins and aliphatic betaines such as lauryl betaine; cationic types, including the long chain $C_{12}$–$C_{22}$ dialiphatic, short chain $C_1$–$C_4$ dialiphatic quaternary ammonium salts such as ditallow dimethyl ammonium chloride, bistridecyl dimethyl ammonium chloride, and ditallow dimethyl ammonium methylsulfate, the long chain $C_{12}$–$C_{22}$ dialkanoyl(alkenoyl) -2-hydroxyethyl, short chain $C_1$–$C_4$ dialiphatic quaternary ammonium salts such as ditallowoyl-2-hydroxyethyl dimethyl ammonium chloride, the long chain $C_{12}$–$C_{22}$ dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate, the short chain $C_1$–$C_4$ dialiphatic, long chain $C_{12}$–$C_{22}$ monoaliphatic benzyl quaternary ammonium salts such as dimethyl stearyl benzyl ammonium chloride and dimethyl tallow benzyl ammonium chloride, the long chain $C_{12}$–$C_{22}$ dialkoyl(alkenoyl)-2-aminoethyl, short chain $C_1$–$C_4$ monoaliphatic, short chain $C_1$–$C_4$ monohydroxyaliphatic quaternary ammonium salts such as ditallowoyl-2-aminoethyl methyl 2-hydroxypropyl ammonium methyl sulfate and dioleoyl-2-aminoethyl methyl 2-hydroxyethyl ammonium methyl sulfate; anionic types including the dialiphatic esters of sodium sulfosuccinic acid such as the dioctyl ester of sodium sulfosuccinic acid and the bistridecyl ester of sodium sulfosuccinic acid, the amine salts of dodecylbenzene sulfonic acid; and mixtures of these secondary emulsifiers. These secondary emulsifiers can be obtained commercially or prepared using methods known in the art. The preferred secondary emulsifiers are ditallow dimethyl ammonium methyl sulfate and ditallow dimethyl ammonium methyl chloride. When these optional secondary emulsifiers are included in the emulsifier component, it is typically at a weight ratio of primary to secondary emulsifier of from about 50:1 to about 1:4, preferably from about 30:1 to about 2:1.

The oil phase used to form the HIPEs comprises from about 85 to about 98% by weight monomer component and from about 2 to about 15% by weight emulsifier component. Preferably, the oil phase will comprise from about 90 to about 97% by weight monomer component and from about 3 to about 10% by weight emulsifier component. The oil phase also can contain other optional components. One such optional component is an oil soluble polymerization initiator of the general type well known to those skilled in the art, such as described in U.S. Pat. No. 5,290,820 (Bass et al), issued Mar. 1, 1994, which is incorporated by reference.

A preferred optional component is an antioxidant such as a Hindered Amine Light Stabilizer (HALS) such as bis-(1, 2,2,5,5-pentamethylpiperidinyl) sebacate (Tinuvin-765®) or a Hindered Phenolic Stabilizer (HPS) such as Irganox-1076® and t-butylhydroxyquinone. Another optional component is a plasticizer such as dioctyl azelate, dioctyl sebacate or dioctyl adipate. Other optional components include fillers, colorants, fluorescent agents, opacifying agents, chain transfer agents, and the like. Certain of these components may be incorporated selectively within one oil phase or the other wherein two oil phases are used to form the heterogeneous HIPE and subsequent foam as described hereinafter.

2. Water Phase Components

The discontinuous water internal phase of the HIPE(s) is generally an aqueous solution containing one or more dissolved components. One essential dissolved component of the water phase is a water-soluble electrolyte. The dissolved electrolyte minimizes the tendency of monomers, comonomers, and crosslinkers that are primarily oil soluble to also dissolve in the water phase. This, in turn, is believed to minimize the extent to which polymeric material fills the cell windows at the oil/water interfaces formed by the water phase droplets during polymerization. Thus, the presence of electrolyte and the resulting ionic strength of the water phase is believed to determine whether and to what degree the resulting preferred polymeric foams can be open-celled.

Any electrolyte capable of imparting ionic strength to the water phase can be used. Preferred electrolytes are mono-, di-, or trivalent inorganic salts such as the water-soluble halides, e.g., chlorides, nitrates and sulfates of alkali metals and alkaline earth metals. Examples include sodium chloride, calcium chloride, sodium sulfate and magnesium sulfate. Calcium chloride is the most preferred for use in the present invention. Generally the electrolyte will be utilized in the water phase of the HIPE(s) in a concentration in the range of from about 0.2 to about 20% by weight of the water phase. More preferably, the electrolyte will comprise from about 1 to about 10% by weight of the water phase, and most preferably from about 2 to about 5% by weight of the water phase.

The HIPE(s) will also typically contain an effective amount of a polymerization initiator. Such an initiator component is generally added to the water phase of the HIPE(s) and can be any conventional water-soluble free radical initiator. These include peroxygen compounds such as sodium, potassium and ammonium persulfates, hydrogen peroxide, peroxyacetic acid, sodium perborate, potassium monopersulfate, sodium percarbonate and the like. Conventional redox initiator systems can also be used. Such systems are formed by combining the foregoing peroxygen compounds with reducing agents such as sodium bisulfite, L-ascorbic acid or ferrous salts.

The initiator can be present at up to about 20 mole percent based on the total moles of polymerizable monomers present in the oil phase. More preferably, the initiator is present in an amount of from about 0.001 to about 10 mole percent based on the total moles of polymerizable monomers in the oil phase.

3. Hydrophilizing Surfactants and Hydratable Salts

The polymer forming the HIPE foam structure may preferably be substantially free of polar functional groups. This means the polymeric foam will be relatively hydrophobic in character. These hydrophobic foams can find utility where the absorption of hydrophobic fluids is desired, or where water resistance is desired (e.g., in filtering or sound deadening applications, for example). Uses of this sort include those where an oily component is mixed with water and it is desired to separate and isolate the oily component, such as in the case of oil spills.

When these foams are to be used as absorbents for aqueous fluids such as juice spills, milk, blood, and urine, they generally require treatment to render the foam relatively more hydrophilic. This can be accomplished by treating the HIPE foam with a hydrophilizing surfactant in a manner described more fully hereafter.

These hydrophilizing surfactants can be any material that enhances the water wettability of the polymeric foam surface. They are well known in the art, and can include a variety of surfactants, preferably of the nonionic type. They will generally be in a liquid form, and can be dissolved or dispersed in a hydrophilizing solution that is applied to the HIPE foam surface. In this manner, hydrophilizing surfactants can be adsorbed by the preferred HIPE foams in amounts suitable for rendering the surfaces thereof substantially hydrophilic, but without substantially impairing the desired flexibility and compression deflection characteristics of the foam. Such surfactants can include all of those previously described for use as the oil phase emulsifier for the HIPE, such as diglycerol monooleate, sorbitan monooleate and diglycerol monoisostearate. Such hydrophilizing surfactants can be incorporated into the foam during HIPE formation and polymerization, or can be incorporated by treatment of the polymeric foam with a solution or suspension of the surfactant in a suitable carrier or solvent. In preferred foams, the hydrophilizing surfactant is incorporated such that residual amounts of the surfactant that remain in the foam structure are in the range from about 0.5 to about 10%, preferably from about 0.5 to about 6%, by weight of the foam.

Another material that is typically incorporated into the HIPE foam structure is a hydratable, and preferably hygroscopic or deliquescent, water soluble inorganic salt. Such salts include, for example, toxicologically acceptable alkaline earth metal salts. Salts of this type and their use with oil-soluble surfactants as the foam hydrophilizing agent is described in greater detail in U.S. Pat. No. 5,352,711 (DesMarais), issued Oct. 4, 1994, the disclosure of which is incorporated by reference. Preferred salts of this type include the calcium halides such as calcium chloride that, as previously noted, can also be employed as the water phase electrolyte in the HIPE.

Hydratable inorganic salts can easily be incorporated by treating the foams with aqueous solutions of such salts. These salt solutions can generally be used to treat the foams after completion of, or as part of, the process of removing the residual water phase from the just-polymerized foams. Treatment of foams with such solutions preferably deposits hydratable inorganic salts such as calcium chloride in residual amounts of at least about 0.01% by weight of the foam, and typically in the range of from about 0.01 to about 12%, preferably from about 0.01 to about 5%, by weight of the foam. Treatment of these relatively hydrophobic foams with hydrophilizing surfactants (with or without hydratable salts) will typically be carried out to the extent necessary to impart suitable hydrophilicity to the foam. For example, the foams may be washed in a solution of 0.5% Pegosperse 200 ML and 0.05% calcium chloride to produce a completely wettable foam. Some foams of the preferred HIPE type, however, are suitably hydrophilic as prepared, and can have incorporated therein sufficient amounts of hydratable salts, thus requiring no additional treatment with hydrophilizing surfactants or hydratable salts. In particular, such preferred HIPE foams include those where certain oil phase emulsifiers previously described and calcium chloride are used in the HIPE. In those instances, the polymeric foam will be suitably hydrophilic, and will include residual water-phase liquid containing or depositing sufficient amounts of calcium chloride to render the foam hydrophilic, even after the polymeric foam has been dewatered or dried as described hereafter.

B. Processing Conditions for Obtaining HIPE Heterogeneous Foams

Foam preparation typically involves the steps of: 1) forming two distinct high internal phase emulsions; and 2) either (a) combining the two emulsions prior to polymerization of either emulsion and then polymerizing the oil phase of both emulsions simultaneously, or (b) partly or completely polymerizing the oil phase of one of the emulsions, combining the resulting polymer with the other emulsion, followed by polymerizing the second emulsion and the first emulsion, if combined when partly cured. Alternatively, foam preparation my comprise 1) forming a single emulsion and rhythmically or continuously varying conditions such as shear rate, pour temperature, etc.; and 2) polymerizing the resulting emulsion. In either case, optional steps include 3) washing the solid polymeric foam structure to remove the original residual water phase from the foam and, if necessary, treating the foam with a hydrophilizing surfactant and/or hydratable salt to deposit any needed hydrophilizing surfactant/hydratable salt, and 4) thereafter dewatering this polymeric foam structure.

The general procedures for HIPE formation, polymer curing, foam washing and foam dewatering are described in U.S. Pat. No. 5,387,207 (Dyer et al.) issued Feb. 7, 1995 and U.S. Pat. No. 5,149,720 (DesMarais et al), issued Sep. 22, 1992, which are incorporated by reference. Though not specifically discussed in the U.S. Pat. No. 5,387,207, the temperature of the aqueous wash solution can be important. It is generally desired that it be greater than the highest Tg of any distinct region of the foam. See also copending U.S. application Ser. No. 08/370,694, filed Jan. 10, 1995 by T. DesMarais (Case No. 5543) (herein incorporated by reference), which describes an improved continuous process having a recirculation loop for the HIPEs. The use of such a recirculation loop in preparing the present foams is primarily useful when the distinct emulsions are poured from distinct mixing heads.

III. Uses of Polymeric Foams

A. In General

Heterogeneous polymeric foams according to the present invention are broadly useful as in applications involving energy dissipation (e.g. acoustic and mechanical insulation), thermal insulation (see co-pending U.S. application Ser. No. 08/472,447, filed Jun. 7, 1995 by Dyer et al., and 08/484,727, filed Jun. 7, 1995 by DesMarais et al., both of which are incorporated by reference herein), filtration, and absorbent cores in absorbent articles. These foams can also be employed as environmental waste oil sorbents, as absorbent components in bandages or dressings, to apply paint to various surfaces, in dust mop heads, in wet mop heads, in dispensers of fluids, in packaging, in shoes, in odor/moisture sorbents, in cushions, in gloves, and for many other uses.

B. Absorbent Articles

The heterogeneous polymeric foams of the present invention are particularly useful as at least a portion of the absorbent structures (e.g., absorbent cores) for various absorbent articles. Use of the term "absorbent article" herein is meant a consumer product that is capable of absorbing significant quantities of urine or other fluids (i.e., liquids), like aqueous fecal matter (runny bowel movements), discharged by an incontinent wearer or user of the article. Examples of such absorbent articles include disposable diapers, incontinence garments, catamenials such as tampons and sanitary napkins, disposable training pants, bed pads, and the like. The absorbent foam structures herein are particularly suitable for use in articles such as diapers, incontinence pads or garments, clothing shields, and the like. Structures of representative absorbent articles such as infant diapers are described in more detail in U.S. Pat. No. 5,387,207 (Dyer et al.) issued Feb. 7, 1995. The alternative materials and embodiments described therein are equally applicable to the present invention.

Figure 14:
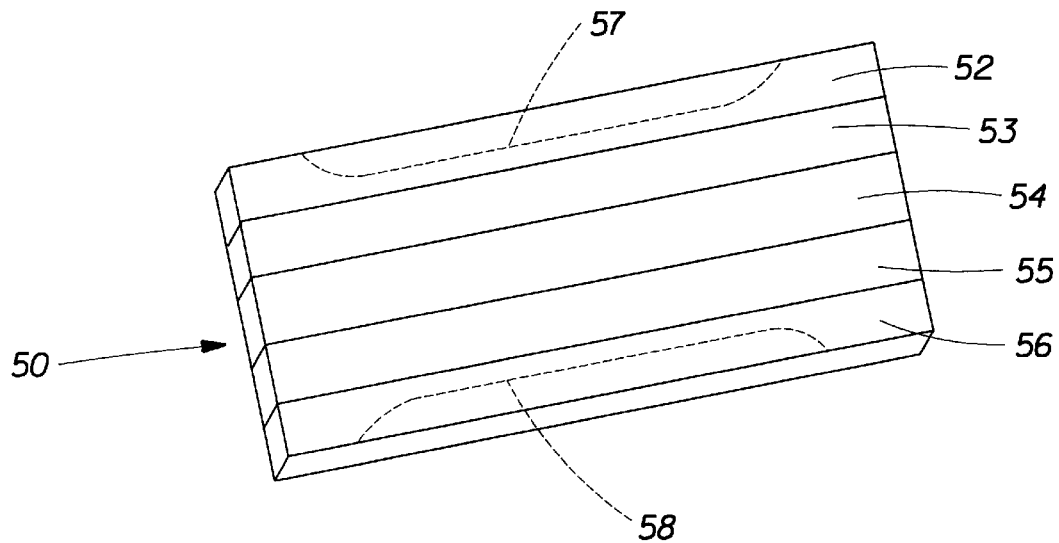
FIG. 14 of the drawings is a perspective view of a single piece of heterogeneous foam of the present invention having 5 distinct regions.
Figure 15:
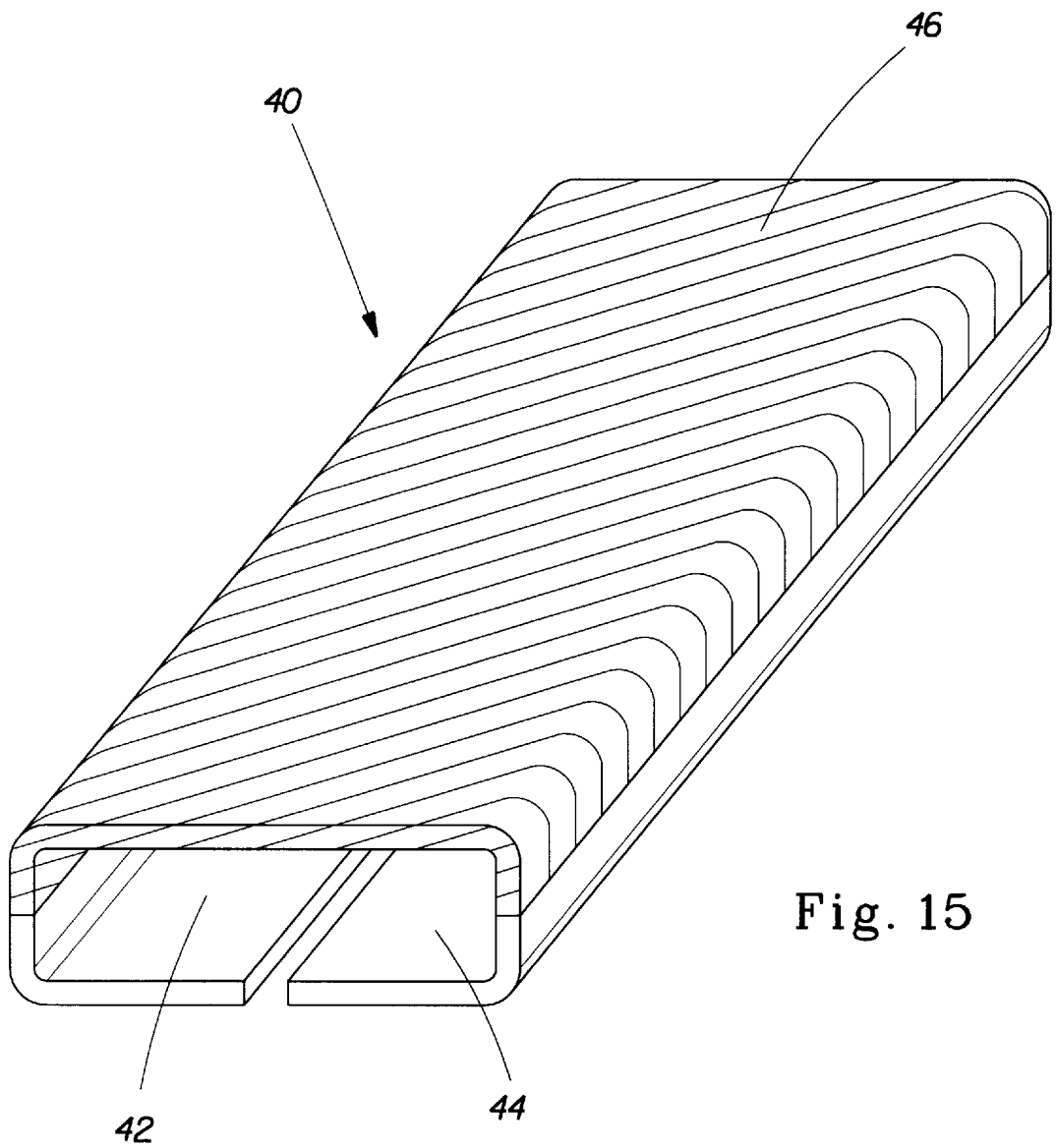
FIG. 15 of the drawings is a perspective view of the same foam structure as that depicted in FIG. 13, where the foam is c-folded so as to provide a structure having a relatively large celled structure on the top and a relatively small celled structure on the bottom. This foam structure is particularly suited for use an absorbent article such as a catamenial pad, and provides both an acquisition/distribution layer and a storage layer in one piece of foam.

Multi-layer absorbent cores can also be made according to copending U.S. application Ser. No. 08/521,556 (Gary Dean Lavon et al), filed Aug. 30, 1995 (Case No. 5547R) (herein incorporated by reference), where the fluid storage/redistribution layer comprises an absorbent foam according to the present invention. One object of the present invention is to simplify the number of discrete layers of foam that must be used to form these multilayer composites. For example, a foam as depicted in FIG. 13 with an acquisition type material in region 46 and a storage type material in regions 42 and 44 may be C-wrapped to deliver a multilayer design from a single piece of heterogeneous foam. Alternatively, a foam as depicted in FIG. 14 wherein regions 52 and 56 are of suitable width, microstructure and surface area per volume to serve as an acquisition material and regions 53, 54, and 55 are of suitable width, microstructure and surface area per volume to serve as a storage material can be S-wrapped to produced a storage core of 5 layers from a single piece of heterogeneous foam.

Figure 10:
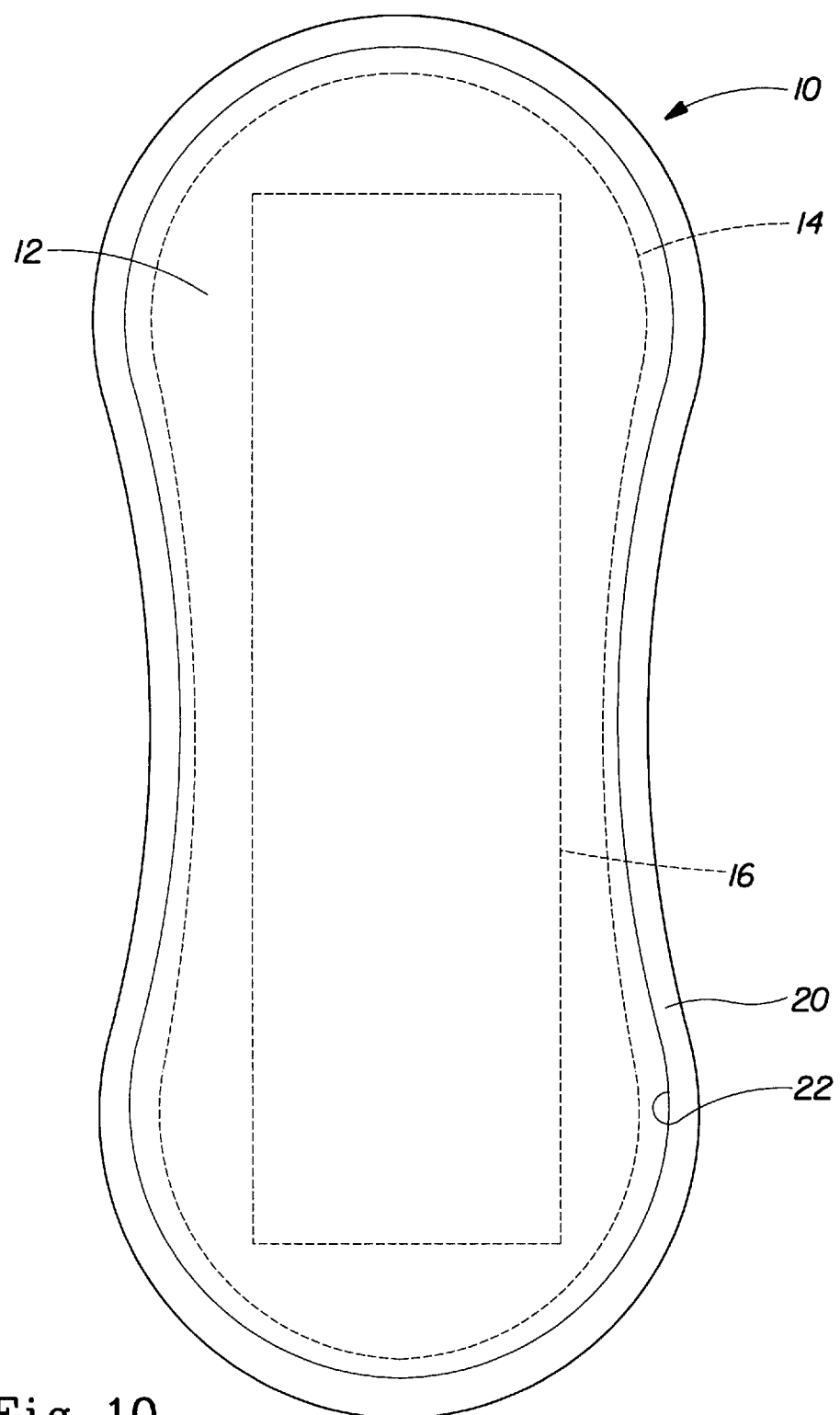
FIG. 10 is a top-plan view of a catamenial product having a heterogeneous foam of the present invention as an absorbent member.

In another embodiment, an article containing a heterogeneous foam of the present invention is a catamenial pad depicted in FIG. 10. This catamenial pad 10 is constructed of fluid pervious primary topsheet 12, an absorbent core consisting of an optional fluid acquisition layer 14 commonly referred to as a "secondary topsheet", a fluid storage absorbent member 16 made of one or more polymeric foams according to the present invention, and a fluid impervious backsheet 18. The backsheet 18 and the topsheet 12 are positioned adjacent the garment surface and the body surface, respectively, of pad 10 and are preferably joined to each other. For example, the backsheet 18 and the topsheet 12 can be secured to each other by adhesive.

The backsheet 18 is impervious to fluids (e.g., menses) and is preferably manufactured from a thin plastic film, although other flexible liquid impervious materials may also be used. As used herein, the term "flexible" refers to materials that are compliant and will readily conform to the general shape and contours of the human body. The backsheet 18 prevents the exudates absorbed and contained in the absorbent structure from wetting articles that contact the sanitary napkin 10 such as pants, pajamas and undergarments. The backsheet 18 can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 18 can permit vapors to escape from the absorbent core (i.e., is breathable) while still preventing exudates from passing through the backsheet 18.

The topsheet 12 is compliant, soft feeling, and non-irritating to the wearer's skin. Further, the topsheet 12 is fluid pervious permitting fluids (e.g., menses) to readily penetrate through its thickness. A suitable topsheet 12 can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Preferred topsheets for use in the present invention are selected from high loft nonwoven topsheets and aperture formed film topsheets. Apertured formed films are especially preferred for the topsheet because they are pervious to body exudates and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Particularly preferred microapertured formed film topsheets are disclosed in U.S. Pat. No. 4,609,518 (Curro et al), issue Sep. 2, 1986 and U.S. Pat. No. 4,629,643 (Curro et al), issued Dec. 16, 1986, which are incorporated by reference. The preferred topsheet for the present invention is the formed film described in one or more of the above patents and marketed on sanitary napkins by The Procter & Gamble Company of Cincinnati, Ohio as "DRI-WEAVE."

The body surface of the formed film topsheet can be hydrophilic so as to help liquid to transfer through the topsheet faster than if the body surface was not hydrophilic so as to diminish the likelihood that menstrual fluid will flow off the topsheet rather than flowing into and being absorbed by the absorbent structure. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated by reference. Alternatively, the body surface of the topsheet can be made hydrophilic by treating it with a surfactant such as is described in the above referenced U.S. Pat No. 4,950,254, incorporated herein by reference.

In use, pad 10 can be held in place by any support or attachment device (not shown) well-known for such purposes. Preferably, pad 10 is placed in the user's undergarment or panty and secured thereto by a fastener such as an adhesive. The adhesive provides a means for securing the pad in the crotch portion of the panty. Thus, a portion or all of the outer surface of the backsheet 18 is coated with adhesive. Any adhesive or glue used in the art for such purposes can be used for the adhesive herein, with pressure-sensitive adhesives being preferred. Before pad 10 is placed in use, the pressure-sensitive adhesive is typically covered with a removable release liner in order to keep the adhesive from drying out or adhering to a surface other than the crotch portion of the panty prior to use.

Figure 11:
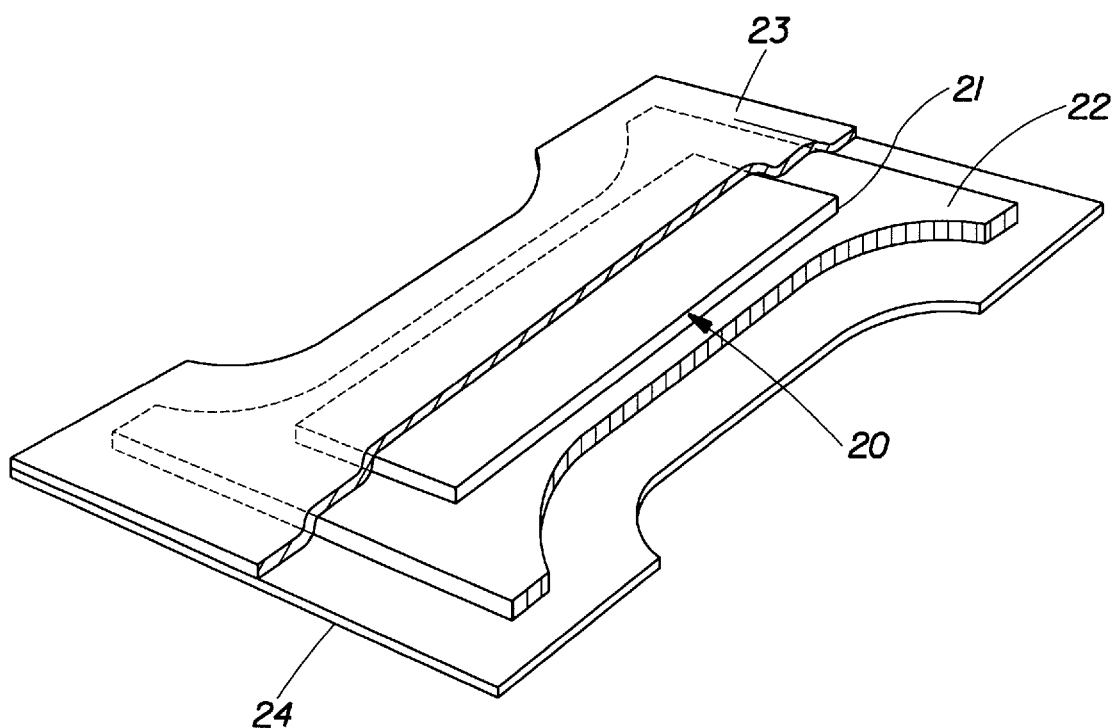
FIG. 11 is a cutaway depiction of a disposable diaper that utilizes the absorbent polymeric foam of the present invention as an hourglass-shaped fluid storage/distribution component, optionally in an absorbent diaper core of dual-layer configuration.

In another embodiment, an article containing a heterogeneous foam of the present invention is a disposable diaper. Disposable diapers comprising the absorbent foam structures of the present invention can be made by using conventional diaper making techniques, but by replacing or supplementing the wood pulp fiber web ("airfelt") or modified cellulosic core absorbents typically used in conventional diapers with one or more foam structures of the present invention. Foam structures of the present invention can thus be used in diapers in single layer, or in various multiple layer core configurations as previously described. A representative disposable diaper embodiment of the present invention is illustrated by FIG. 11 of the drawings. Such a diaper includes an absorbent core 20, comprising an optional upper fluid acquisition layer 21, and an underlying fluid storage/redistribution layer 22 comprising an absorbent heterogeneous foam structure of the present invention. A topsheet 23 is superposed and co-extensive with one face of the core, and a liquid impervious backsheet 24 is superposed and coextensive with the face of the core opposite the face covered by the topsheet. The backsheet most preferably has a width greater than that of the core thereby providing side marginal portions of the backsheet which extend beyond the core. The diaper is preferably constructed in an hourglass configuration.

Another type of absorbent article which can utilize the absorbent foam structures of the present invention comprises form-fitting products such as training pants. Such form-fitting articles will generally include a nonwoven, flexible substrate fashioned into a chassis in the form of briefs or shorts. An absorbent foam structure according to the present invention can then be affixed in the crotch area of such a chassis in order to serve as an absorbent "core". This absorbent core will frequently be over-wrapped with envelope tissue or other liquid pervious, nonwoven material. Such core overwrapping thus serves as the "topsheet" for the form-fitting absorbent article.

The flexible substrate which forms the chassis of the form-fitting article can comprise cloth or paper or other kinds of nonwoven substrate or formed films and can be elasticized or otherwise stretchable. Leg bands or waist bands of such training pants articles can be elasticized in conventional fashion to improve fit of the article. Such a substrate will generally be rendered relatively liquid-impervious, or at least not readily liquid-pervious, by treating or coating one surface thereof or by laminating this flexible substrate with another relatively liquid-impervious substrate to thereby render the total chassis relatively liquid-impervious. In this instance, the chassis itself serves as the "backsheet" for the form-fitting article. Typical training pants products of this kind are described in U.S. Pat. No. 4,619,649 (Roberts), issued Oct. 28, 1986, which is incorporated by reference.

Figure 12:
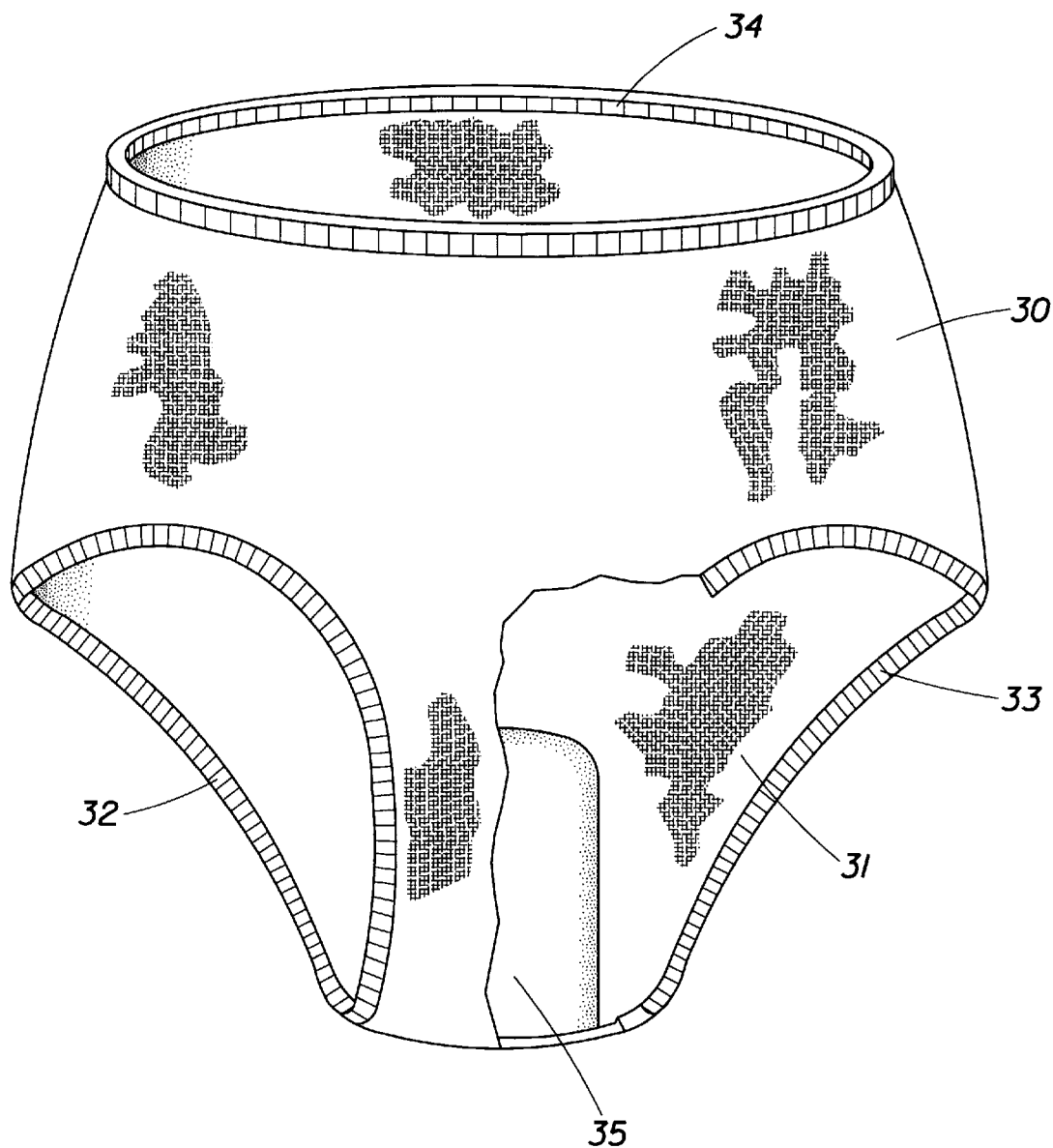
FIG. 12 of the drawings represents a cut-away view of a form-fitting article such as a disposable training pants product that employs an absorbent polymeric foam according to the present invention as an absorbent core.

A typical form-fitting article in the form of a disposable training pants product is shown in FIG. 12 of the drawings. Such a product comprises an outer layer 30 affixed to a lining layer 31 by adhesion along the peripheral zones thereof. For example, the inner lining 31 can be affixed to the outer layer 30, along the periphery of one leg band area 32, along the periphery of the other leg band area 33, and along the periphery of waistband area 34. Affixed to the crotch area of the article is a generally rectangular absorbent core 35 comprising an absorbent heterogeneous foam structure of the present invention.

C. Composite Foams

As discussed above, numerous possibilities exist with regard to arrangement of the discrete regions within a given composite foam. The skilled artisan will recognize that in light of the teachings herein, routine experimentation will provide foams having various qualities, depending on the desired end-use. As such, though four representative foam embodiments are depicted and discussed in FIGS. 13, 14, 16, and 17/18, it is not intended that the scope of the invention is in any way limited to these embodiments.

Referring to FIG. 13, a heterogeneous foam 40 having repeating stripes is depicted. In particular, foam piece 40 has a region 46 of relatively large-celled material, positioned between two regions 42 and 44, both of relatively smaller celled material. Regions 42 and 44 may be either the same, or they may be different. As depicted rectangularly, foam piece 40 is suited for use as an absorbent core for a catamenial product. The relatively large celled region 46 will allow for rapid acquistion and distribution of discharged body fluid, while small celled regions 42 and 44 will prevent leakage at the sides of the product. Arcuate lines 47 and 48 depict optional cut-out regions that may be preferred where foam piece 40 is used as an absorbent core material in a diaper. Alternatively, or in addition, the acquistion/distribution region 46 may have a relatively lower specific area per volume than storage regions 42 and 44.

The foam depicted in FIG. 14 is similar to that shown in FIG. 13, but has five distinct regions instead of three. In a preferred embodiment, center region 54 will comprise relatively large celled material, which is suited for rapid acquisition of body fluid. Outer regions 52 and 56 will preferably comprise relatively small celled material, again to prevent leakage of fluid from the sides of the corresponding product.

Regions 53 and 55 will both preferably comprise material that have cell sizes smaller than region 54, but larger than regions 52 and 56. As a core for a feminine hygiene pad, outer regions 52 and 56 may have hole sizes smaller than 8 μm to preclude passage of red blood cells into the outer edges of the product which might signal impending side-leakage and failure to the consumer. Such regions will absorb free fluid from the menses without passing red blood cells and attendant color.

The foam depicted in FIGS. 17 and 18 is illustrative of an embodiment where the distinct regions are layered in the z-direction. FIG. 17 is a side view of foam 70 having upper region 72 and lower region 74. FIG. 18 is a perspective view, again showing upper region 72 and lower region 74. This type of foam is particularly suitable as an absorbent material, such as a diaper, wherein upper region 72 is an acquisition material, and lower region 74 is a storage material. A foam having regions layered in the z-direction can be formed by pouring an emulsion to form region 74 in a mold, and simultaneously or sequentially adding a second emulsion to form region 72. In a preferred embodiment, region 72 will have a relatively lower specific surface area per volume than region 74, which will allow region 74 to drain fluid from region 72.

IV. Test Methods

Many of the test methods used require a larger sample of homogeneous material than may be present in the heterogeneous foams of the present invention. Measurement of the properties of the distinct regions must then be obtained by taking a sample of the distinct emulsion streams, curing them identically, and using them to determine the specific independent properties of the heterogeneous regions of the foam.

A. Dynamic Mechanical Analysis (DMA)

DMA is used to determine the Tgs of polymers including polymeric foams. Samples of the foams are sliced into blocks 3–5 mm in thickness and washed 3–4 times in distilled water, expressing the fluid through roller nips between each washing. The resulting foam blocks are allowed to dry in air. The dried foam slices are cored to yield a cylinders 25 mm in diameter. These cylinders are analyzed using a Rheometrics RSA-II dynamic mechanical analyzer set in compression mode using parallel plates 25 mm in diameter. Instrument parameters used were as follows:

- Temperature step from ca. 85° C. to −40° C. in steps of 2.5° C.
- Soak intervals between temperature changes of 125–160 seconds
- Dynamic strain set at 0.1% to 1.0% (usually 0.7%)
- Frequency set at 1.0 radians/second
- Autotension set in static force tracking dynamic force mode with initial static force set at 5 g.

The glass transition temperature is taken as the maximum point of the loss tangent versus temperature curve. Tg is appropriately measured only on a homogeneous portion of the heterogeneous foam, or from a representative piece of homogeneous foam prepared under the same conditions as the region from the heterogeneous foam.

B. Resistance to Compression Deflection (RTCD)

Resistance to compression deflection can be quantified by measuring the amount of strain (% reduction in thickness) produced in a foam sample which has been saturated and expanded with synthetic urine, after a confining pressure of 0.74 psi (5.1 kPa) has been applied to the sample as described in the TEST METHODS section of U.S. Pat. No. 5,387,207 (Dyer et al.) issued Feb. 7, 1995. Resistance to Compression Deflection measurements are typically made on the same sample concurrently with the measurement of Free Absorbent Capacity and Expansion Factor as described below.

C. Free Absorbent Capacity

Free absorbent capacity can be quantified by measuring the amount of synthetic urine absorbed in a foam sample which has been saturated and expanded with synthetic urine. Free Absorbent Capacity measurements are typically made on the same sample concurrently with the measurement of Resistance to Compression Deflection and Expansion Factor as described in the TEST METHODS section of U.S. Pat. No. 5,387,207 (Dyer et al.) issued Feb. 7, 1995.

D. Interfacial tension (IFT) method (Spinning Drop)

Interfacial Tension (IFT) is measured at 50° C. by the spinning drop method described in U.S. Pat. No. 5,387,207 (Dyer et al.) issued Feb. 7, 1995, (herein incorporated by reference), except that: (1) the monomer mixture used in preparing the oil phase contains styrene, divinylbenzene (55% technical grade), 2-ethylhexylacrylate, and 1,4-butanediol dimethacrylate in a weight ratio of 14:14:60:12; (2) the concentration of emulsifier in the oil phase is varied by dilution from an upper concentration of generally about 5–10 weight % down to a concentration where the IFT increases to a value that is at least about 10 dyne/cm greater than the minimum IFT, or about 18 dyne/cm, whichever is less; (3) a smooth line drawn through a plot of IFT versus log emulsifier concentration is used to determine the minimum IFT; (4) the Critical Aggregation Concentration (CAC) is determined by extrapolating the low-concentration, generally linear portion of the IFT versus log concentration plot (i.e., the portion of the curve typically used to calculate surface area per molecule at the interface, see for example Rosen, M. J. "Surfactants and Interfacial Phenomena"; 2nd ed.; Wiley & Sons: New York, 1989; pp 64–69) to higher concentration; the emulsifier concentration on this extrapolated line corresponding to the minimum IFT is taken as the CAC. Generally, an upper emulsifier concentration of about 5–10 weight % is used. Desirably, the upper emulsifier concentration used is at least about twice (more desirably at least about three times) the CAC of the emulsifier. For emulsifiers having a solubility in the oil phase at ambient-temperature of less than 5 wt. %, the upper concentration limit can be reduced as long as this concentration is still at least about twice the CAC of the emulsifier at 50° C.

E. Capillary Absorption Pressures

A capillary absorption isotherm curve is generated using the Vertical Wicking Absorbent Capacity test described in the TEST METHODS section of U.S. Pat. No. 5,387,207 (Dyer et al.) issued Feb. 7, 1995, which is incorporated by reference, except at 31° C. rather than 37° C. The curve is a plot of the absorbent capacity of each segment as a function of wicked height, using the distance from the top of the water reservoir to the midpoint of each segment for the height h. The capillary absorption pressure is taken as the height of the foam that has an absorbent capacity one-half of the foam's free absorbent capacity.

V. Specific Examples

These examples illustrate the specific preparation of foams from HIPEs according to the present invention.

EXAMPLE 1

Preparation of a Heterogeneous Foam from Two HIPE Streams HIPE Preparation

An aqueous phase is prepared containing the ingredients shown in Table 1. Two organic phases are prepared using the ingredients shown in Tables 2and 3.

TABLE 1

Aqueous Phase Composition for HIPE.

| | | |
|---|---|---|
| Water | 756 L | |
| Potassium Persulfate | 378 g | 0.05% |
| Calcium Chloride | 72,640 g | 10.0% |

TABLE 2

First Organic Phase Composition for HIPE.

| | | |
|---|---|---|
| 2-ethylhexyl acrylate | 2,900 g | 58% |
| divinyl benzene* | 2,520 g | 42% |
| diglycerol monooleate | 360 g | 6%** |
| Tinuvin 765 | 30 g | 0.5% |

*Divinyl benzene in this and later tables is a special blend comprising 60% ethyl styrene and 40% divinyl benzene, unless otherwise specified.
**Addition level of emulsifier and other adjuvants to the oil phase are "add-on" percentages; monomer composition sums to 100%.

TABLE 3

Second Organic Phase Composition for HIPE.

| | | |
|---|---|---|
| 2-ethylhexyl acrylate | 2,400 g | 40% |
| divinyl benzene | 3,600 g | 60% |
| diglycerol monooleate | 360 g | 6%** |
| Tinuvin 765 | 30 g | 0.5% |

(Tinuvin 765 is bis(1,2,2,5,5-pentamethylpiperidinyl) sebacate. This diglycerol monooleate emulsifier is prepared following the general procedure for preparing polyglycerol esters described in U.S. Pat. No. 5,387,207 (Dyer et al.) issued Feb. 7, 1995. A polyglycerol composition comprising approximately 97% or greater diglycerol and 3% or less triglycerol (Solvay Performance Chemicals; Greenwich, Conn.) is esterified with fatty acids having a fatty acid composition comprising approximately 71% C18:1, 4% C18:2, 9% C16:1, 5% C16:0, and 11% other fatty acids (Emersol-233LL, Emery/Henkel) in a polyglycerol:fatty acid weight ratio of approximately 60:40, using sodium hydroxide as a catalyst at about 225° C. under conditions of mechanical agitation, nitrogen sparging, and gradually increasing vacuum, with subsequent phosphoric acid neutralization, cooling to about 85° C., and settling to reduce the level of unreacted polyglycerols. The polyglycerol ester reaction product is first fractionally distilled through two CMS-15A centrifugal molecular stills connected in series to reduce the levels of unreacted polyglycerols and fatty acids and then redistilled through the stills to yield distillation fractions high in diglycerol monoesters. Typical conditions for the final distillation pass are a feed rate of about 15 lb/hr, a degasser vacuum of about 21–26 microns, a bell jar vacuum of about 6–12 microns, a feed temperature of about 170° C., and a residue temperature of about 180° C. Distillation fractions high in diglycerol monoesters are combined, yielding a reaction product (as determined by supercritical fluid chromatography) comprising approximately 50% diglycerol monooleate, 27% other diglycerol monoesters, 20% polyglycerols, and 3% other polyglycerol esters. The resultant diglycerol monooleate emulsifier imparts a minimum oil phase/water phase interfacial tension value of approximately 1.0 dyne/cm and has a critical aggregation concentration of approximately 0.9 wt %. After mixing, the reaction product is allowed to settle overnight. The supernatant is withdrawn and used in the oil phase as the emulsifier in forming the HIPE. (About 20 g of a sticky residue is discarded.))

Separate streams of the two oil phases (25° C.) and divided water phase are fed to separate dynamic mixing apparati, described in more detail in U.S. Pat. No. 5,387,207 (Dyer et al.) issued Feb. 7, 1995. Appropriate mixing of the separate combined streams in the dynamic mixing apparati is achieved by means of separate pin impellers in separate mixing cylinders.

Separate HIPEs are made from the two oil phases described above and separated streams of the common water phase (also above) and delivered into a vessel, typically a round polypropylene tub, 17 in. (43 cm) in diameter and 7.5 in. (10 cm) high, with a concentric insert made of Celcon plastic which is rotating beneath the exit nozzles of the two mixing chambers. The insert is 5 in. (12.7 cm) in diameter at its base and 4.75 in. (12 cm) in diameter at its top and is 6.75 in. (17.14 cm) high. The vessel is filled to about 0.5 inches from the top and the polymer is cured in a room maintained at 65° C. for up to 18 hours. The geometry of this specific filling scheme results in sequential layers of HIPE from the two nozzles being delivered on top of each other making in the resulting foam stripes of one region integrally meshed with stripes of the second, etc. region(s). Wherein the HIPE viscosity is high, an appropriately shaped spreader device may be attached to the exit nozzle to assure even delivery of the HIPE into the vessel. The number of stripes formed is controlled by the rate of pouring as a function of the rate of turning of the receiving tub and its volume, so as to deliver controllably foams that can be cut to provide foam composites illustrated in FIGS. 13 and 14, for example. The relative thickness of each stripe is controlled by the relative rate of delivery of HIPE from each emulsion nozzle. In this specific example, the HIPE stream from Table 2 is delivered at 10 lb/min. with its dynamic pin impeller operating at 1200 rpm and a pour temperature of 54° C. at a water:oil ratio of 50:1 using the triangular spreader on the exit to assure even distribution throughout the width of the tub (Region A). The HIPE stream from Table 3 is delivered at 5 lb/min. with its dynamic pin impeller operating at 400 rpm and a pour temperature of 66° C. at a water:oil ratio of 100:1 (Region B). The result after polymerizing, drying and slicing is a foam having alternating slices with the properties described in Table 4.

TABLE 4

| Property | Region A | Region B |
|---|---|---|
| Tg | 0° C. | 70° C. |
| RTCD | 40% | 40% |
| Density | 0.020 g/cc | 0.010 g/cc |
| Mean Cell Diameter | 40 μm | 120 μm |

EXAMPLE 2

Mixing of the Example 1 HIPEs to Form a Chemically Heterogeneous Foam

The HIPE streams described in Example 1 are delivered to the receiving vessel at the same rate and having been prepared using the same conditions of temperature and dynamic mixing. This produces a foam having heterogeneity of a chemical nature while having identical microcellular morphology and water:oil ratios. In a specific example, both streams are mixed at a water-to-oil ratio of 50:1 using the dynamic pin mixer rotating at 1200 rpm at a delivery rate of 6.0 lb/min. into the tub turning at 2 rpm. When cured and sliced as described hereinafter, this produces a foam as shown in FIG. 14 wherein the different regions 40 and 42/44 have Tgs of 0° C. and 70° C. and densities of 0.20 g/cc.

EXAMPLE 3

Mixing of the Example 1 HIPEs to Form a Microstructurally Heterogeneous Foam Two HIPE streams as in Example 1 are delivered to the receiving vessel using different conditions of temperature and dynamic mixing. This produces a foam having heterogeneity of a chemical nature and microcellular morphology. The water:oil ratio is preserved at 50:1 for both HIPE streams to preserve the same density of the foam throughout. In the simplest example, the rates at which each HIPE is formed are identical so that the relative volume ratio occupied by the two chemically different HIPEs will be 50:50. The chemical compositional difference between the two HIPEs results after curing of a polymer having distinct regions where properties such as Tg, stiffness, resistance to compression deflection, and the like are different, as in Example 2. Additionally, the microstructural properties, e.g. cell size, of the distinct region in this case are different. The HIPE using the oil phase from Table 2 is produced as in Example 1. The HIPE using the oil phase from Table 3 is produced at a water-to-oil ratio of 50:1 using the dynamic pin mixer rotating at 400 rpm at a delivery rate of 3.0 lb/min. into the tub turning at 2 rpm. When cured and sliced as described hereinafter, this produces a foam as shown in FIG. 13 wherein the different regions 46 and 42/44 have the properties shown in Table 5.

TABLE 5

| Property | Region 46 | Region 42/44 |
|---|---|---|
| Tg | 0° C. | 60° C. |
| RTCD | 75% | 5% |
| Density | .020 g/cc | .020 g/cc |
| Mean Cell Diameter | 40 μm | 120 μm |

Numerous variations are possible, including one wherein the HIPEs so formed are compositionally identical, e.g., each separate HIPE is made using the oil phase of Table 2, but is formed under different conditions to provide regions within the resulting foam of different density and mean cell diameters with the same chemical composition and Tg throughout.

EXAMPLE 4

Forming a Heterogeneous Foam from a Single HIPE Stream

In this example, a single HIPE is formed using the oil phase from Table 2 in a single mixing apparatus. During the course of filling the cylindrical tub, the shear applied is varied over time. During the initial stages of the fill, the shear rate is 4300 sec$^{-1}$, declining over time at 180 sec$^{-1}$/minute so that the emulsion formed on each successive rotation of the tub has been subjected to progressively less shear. At the end of the fill, the shear rate has declined to 1400 sec$^{-1}$. (See copending U.S. application Ser. No. 08/520,793 (DesMarais, filed Aug. 30, 1995) for a discussion of processing conditions that affect shear rate.) This results in a foam (after curing and slicing) such as that depicted in FIG. 14 wherein layers 52 through 56 exhibit progressively larger cells. The foam of this example is further depicted in the micrographs of FIGS. 1–8.

EXAMPLE 5

Figure 19:
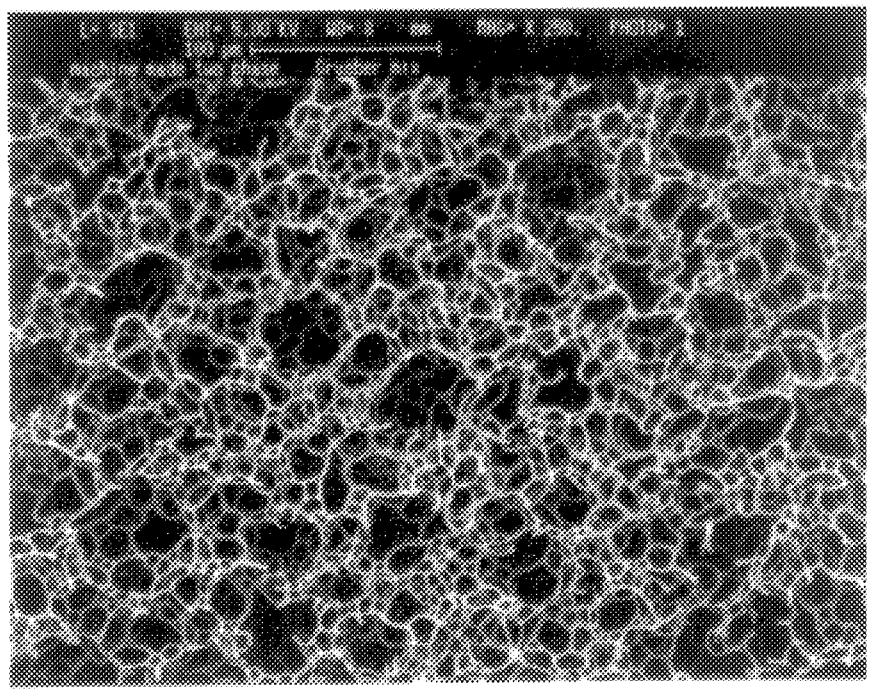
FIG. 19 is a photomicrograph (250× magnification) of a heterogeneous foam having discrete, unconnected regions dispersed in a continuous region. The photomicrograph is believed to be taken at the interface of the continuous and at least one dispersed region. Suprisingly, no discontinuity is observed between the regions.

Forming a Heterogeneous Foam from a Single HIPE Stream Combined with Already Cured HIPE Foam Particulates In this example, a HIPE is produced from the oil stream in Table 3 at a water:oil ratio of 80:1, a dynamic mixer rpm of 400, at 6.0 lb./min. This HIPE is cured as before. The resultant foam is ground into particulate pieces of foam approximately 2 mm in diameter. These pieces of foam still saturated with aqueous phase are then placed in the 17" diameter tub described in Example 2–4 above, approximately half filling the volume of that tub. A second HIPE is produced from the oil phase of Table 2 at a water:oil ratio of 40:1, a dynamic mixer rpm of 400, at 6.0 lb./min. This is delivered into the tub filled with the already formed HIPE foam and blended manually. This mixture is then cured as before. The resulting foam has the structure depicted in FIG. 16 wherein the separated regions 64 comprise the higher Tg, stronger, lower density foam and the continuous region 62 comprises the lower Tg, more flexible, higher density foam. The density of the composite is 0.017 g/cc. The RTCD of this foam is higher than the RTCD of a homogeneous foam made from the oil phase of Table 2. An applied stress compresses the foam until the hard points of region 64 become substantially in contact, wherein further compression is resisted. The flexibility of this foam is higher than the flexibility of a homogeneous foam made from the oil phase of Table 3. Flexibility derives from the continuous region 62 in which the rigid foam elements 64 float without impairing flexibility. Surprisingly, a microscopic examination of foams so made reveals no obvious structural defects at the interface between region 62 and regions 64. (See FIG. 19, which is a photomicrograph believed to be taken at the interface of region 62 and at least one discrete region 64.) The skilled artisan will recognize that because no obvious structural defects are observed at the interface between continuous and dispersed regions, certain process described herein (particularly this Example 5) may be useful in providing a homogeneous foam made with varying amounts of previously formed scrap foam. That is, the pieces of foam referred to above would constitute scrap polymerized foam, and would be combined with an unpolymerized emulsion identical to that originally used to form the scrap foam. Prior to the present invention, such a process would not have been deemed useful to provide homogeneous foams that include preformed scrap material.

In an alternative embodiment for forming a heterogeneous foam of the present invention, two or more HIPEs can be combined with the preformed particulates to provide multiple continuous regions having dispersed therein rigid foam elements.

EXAMPLE 6

A diaper is constructed in accordance with Example II of U.S. Pat. No. 5,387,207 (Dyer et al.) issued Feb. 7, 1995, using as the absorbent storage/distribution layer a heterogeneous foam of any of Examples 1 to 5, above.

EXAMPLE 7

Catamenial Pad Made with Heterogeneous Foam

A foam is prepared essentially as described in Example 3 having thicknesses of the distinct regions based on different cell sizes being approximately 3 cm. The conditions of each region are shown in Table 6 below.

TABLE 6

| Region | RPM | Pour Temperature (°C.) | Approx. Mean Cell Size (μm) | Width of Region (cm) |
| --- | --- | --- | --- | --- |
| 1 | 800 | 66° | 50 | 3 |
| 2 | 400 | 66° | 120 | 3 |
| 3 | 800 | 66° | 50 | 3 |

A continuous piece is sliced 3 cm thick and 9 cm width. The width is cut so as to contain the larger cell size region in the middle bounded on each side by a region of smaller cell sized material. (In practice, the smaller cell sized regions may be poured at such a rate as to make its thickness 6 cm so that pieces can be suitably cut from a wide sheet of such foam.) The continuous piece is taken up on a roll and delivered to the pad making operation where it is folded into a "C"-shape by bending the outer 3 cm segments under the center 3 cm segment. The foam is then cut into a 20 cm length and placed into a pad under a topsheet and on top of a backsheet with appropriate adhesive application so as to secure it within the construction. This provides for a layer having faster fluid to acquisition on top of a layer having greater capillary pressure which can effectively drain fluid from the upper layer as decribed in copending U.S. application Ser. No. 08/542,497, filed Oct. 13, 1995 by Dyer et al (Case No. 5546R), which is incorporated by reference, but constructed from a sheet off a single roll.

EXAMPLE 8

Tampon Made with Heterogeneous Foam

A tampon is constructed from a foam that is prepared essentially as described in Example 3 having thicknesses of the distinct regions based on different cell sizes being approximately 3 cm. The conditions of each region are shown in Table 7 below.

TABLE 7

| Region | RPM | Pour Temperature (°C.) | Approx. Mean Cell Size (μm) | Width of Region (cm) |
| --- | --- | --- | --- | --- |
| 1 | 800 | 66° | 50 | 3 |
| 2 | 400 | 66° | 120 | 3 |

A continuous piece is sliced 1.5 cm thick and 6 cm width. The continuous piece is taken up on a roll and delivered to the tampon core making operation where it is shaped into a tube by curling Region 1 around Region 2. The foam is then cut into a 10 cm length and placed inside an outer fluid permeable topsheet with appropriate adhesive application so as to secure it within the construction. This provides for a layer having faster fluid acquisition outside of a layer having greater capillary pressure which can effectively drain fluid from the upper (outer) layer as decribed in copending U.S. application Ser. No. 08/542,497, filed Oct. 13, 1995 by Dyer et al (Case No. 5546R), but constructed from a single sheet off a single roll.

EXAMPLE 9

A Heterogeneous Foam For Use in Filtration

The foam of Example 4 is sliced to a thickness of 5 mm and washed in water to remove most of the residual salts and then dried. The continuous slices of foam are cut into pieces 10 cm×10 cm and reinforced with an outer cardboard outsert covering the outer 1 cm of the foam on both sides. This outsert protects the edges of the material. This piece is inserted into an air stream passing through a plenum. The coarser celled region entraps larger particulates and passes the air stream with relatively little restriction. The finer celled region entraps smaller particles though it will pass the air stream with greater restriction to its flow.

EXAMPLE 10

A Heterogeneous Foam for Use as Sound Insulation

The foam of Example 5 is sliced to a thickness of 5 mm and washed in water to remove most of the residual salts and then dried. The continuous slices of foam are cut into pieces 20 cm×20 cm. The edges of these pieces may be reinforced if needed as described in Example 9. These pieces are then secured to a wall separating a noisy device from a living space. Because the particulate pieces embedded within this foam will somewhat selectively absorb one frequency and the continuous segment of this foam will somewhat selectively absorb another frequency, a broader frequency absorption profile will be obtained, similar to that which would be obtained from two laminated homogeneous foams made separately from these emulsions.

EXAMPLE 11

Forming a Heterogeneous Foam from Three HIPE Streams

Two HIPES streams are prepared as described in Example 1 from the oil phase described in Table 2. The oil is split into two streams, Stream A and Stream B, to be mixed separately into two HIPEs which are compositionally identical but which have different water droplet sizes. Stream A is mixed through a dynamic pin mixer operating at 400 rpm at 66° C. emulsion temperature at a water:oil ratio of 45:1 at 5 lbs/min. Stream B is mixed through a dynamic pin mixer operating at 1600 rpm and 66° C. emulsion temperature at a water:oil ratio of 60:1 at 10 lbs/min. Stream B is further divided equally into two streams. Rather than being delivered into a rotating tub as described in preceding examples, the three streams are delivered into a long rectangular bed with Stream A being delivered into the center of the sluice and Stream B being delivered into each outer third of the sluice. The rectangular bed is bed 45 cm wide and 30 cm deep on a moving web. The length of the bed is indefinite and can be a continuous loop. The portion of the bed filled with the HIPEs is moved gradually into an oven to maintain the temperature at 66° C. suitable for curing of the HIPEs into a polymer. This produces a billet of HIPE foam of indefinite length from which segments may be cut suitable for use in diapers or catamenials and the like.

In a preferred embodiment, hourglass-shaped diaper segments are sliced to appropriate thickness (e.g., 5 mm) and cut from the web along its width (the 45 cm dimension). These cut segments will have foam suited for rapid fluid acquisition in the crotch region of the diaper and foam suited for storage of the fluid in the back and front regions of the diaper. Fluid introduced into the crotch region will be pulled by capillary force into the front and back regions against the force of gravity.

What is claimed is:

1. A process for making a heterogeneous polymeric foam structure of interconnected open-cells, wherein the foam structure has at least two distinct regions that differ by at least about 20% with regard to one or more of polymer density, polymer competition, surface properties, or microcellular morphology, the process comprising the steps of:

A) forming a first water-in-oil emulsion from:
1) an oil phase comprising:
   a) from about 85 to about 98% by weight of a monomer component capable of forming a copolymer having a Tg of about 95° C. or lower, the monomer component comprising:
      i) from about 20 to about 70% by weight of at least one substantially water-insoluble monofunctional monomer capable of forming an atactic amorphous polymer having a Tg of about 25° C. or lower;
      ii) from about 10 to about 50% by weight of at least one substantially water-insoluble monofunctional comonomer capable of imparting toughness about equivalent to that provided by styrene;
      iii) from about 5 to about 50% by weight of a first substantially water-insoluble, polyfunctional crosslinking agent selected from divinylbenzenes, trivinylbenzenes, divinyltoluenes, divinylxylenes, divinylnaphthalenes divinylalkylbenzenes, divinyiphenanthrenes, divinylbiphenyls, divinyldiphenylmethanes, divinylbenzyls, divinylphenylethers, divinyldiphenylsulfides, divinylfurans, divinylsulfide, divinylsulfone, and mixtures thereof; and
      iv) from 0 to about 15% by weight of a second substantially water-insoluble, polyfunctional crosslinking agent selected from polyfunctional acrylates, methacrylates, acrylamides, methacrylamides, and mixtures thereof; and
   b) from about 2 to about 15% by weight of an emulsifier component which is soluble in the oil phase and which is capable of forming a stable water-in-oil emulsion, the emulsifier component comprising a primary emulsifier having at least about 40% by weight emulsifying components selected from diglycerol monoesters of branched $C_{16}$–$C_{24}$ fatty acids, linear unsaturated $C_{16}$–$C_{22}$ fatty acids, and linear saturated $C_{12}$–$C_{14}$ fatty acids; sorbitan monoesters of branched $C_{16}$–$C_{24}$ fatty acids, linear unsaturated $C_{16}$–$C_{22}$ fatty acids, linear saturated $C_{12}$–$C_{14}$ fatty acids; diglycerol monoaliphatic ethers of branched $C_{16}$–$C_{24}$ alcohols, linear unsaturated $C_{16}$–$C_{22}$ alcohols, and linear saturated $C_{12}$–$C_{14}$ alcohols, and mixtures thereof; and
2) a water phase comprising an aqueous solution containing: (a) from about 0.2 to about 20% by weight of a water-soluble electrolyte; and (b) an effective amount of a polymerization initiator;
3) a volume to weight ratio of water phase to oil phase in the range of from about 20:1 to about 200:1;

B) optionally forming a second, distinct water-in-oil emulsion which is different in at least one respect from the first emulsion, but which comprises materials and ranges selected from those listed in parts A)1), A)2), and A)3); and C) either
1) a) combining the first and second water-in-oil emulsions in a forming vessel prior to polymerizing the monomer components of either of the water-in-oil emulsions; and
   b) polymerizing both emulsions to form a polymeric, heterogenous foam;
2) a) partially or completely polymerizing the monomer components in the oil phase of the first water-in-oil emulsion;
   b) combining the material from step C)2)a) and the second water-in-oil emulsion; and
   c) polymerizing the second emulsion, and the first emulsion if combined when partly cured, to provide a polymeric, heterogeneous foam; or
3) making only the first water-in-oil emulsion while varying the process conditions by which it is formed in a regular fashion using a single emulsion forming head.

2. The process of claim 1, wherein two distinct emulsions are utilized, and wherein the first and second water-in-oil emulsions are combined in a forming vessel prior to polymerizing the monomer components in the oil phase of either of the emulsions.

3. The process of claim 1, wherein two distinct emulsions are utilized, and wherein the monomer components in the oil phase of the first water-in-oil emulsion are partly or completely polymerized prior to being combined with the second emulsion.

4. The process of claim 1, wherein only one water-in-oil emulsion is used to make the heterogeneous foam, and wherein the process conditions are varied in a controlled fashion, either rhythmically or continuously, using a single emulsion forming head.

5. The process of claim 2 wherein the first emulsion comprises at least about 20% more than the second emulsion of the monofunctional monomer capable of forming an atactic amorphous polymer having a Tg of about 25° C. or lower.

6. The process of claim 5 wherein the first emulsion comprises at least about 35% more than the second emulsion of the monofunctional monomer capable of forming an atactic amorphous polymer having a Tg of about 25° C. or lower.

7. The process of claim 2 wherein the first emulsion comprises at least about 20% more than the second emulsion of the first substantially water-insoluble, polyfunctional crosslinking agent.

8. The process of claim 7 wherein the first emulsion comprises at least about 35% more than the second emulsion of the first substantially water-insoluble, polyfunctional crosslinking agent.

9. The process of claim 2 wherein the first emulsion has a water-to-oil ratio that is at least about 20% more than the water-to-oil ratio of the second emulsion.

10. The process of claim 9 wherein the first emulsion has a water-to-oil ratio that is at least about 35% more than the water-to-oil ratio of the second emulsion.

11. The process of claim 2 wherein the first emulsion is prepared such that the mean cell size is at least about 20% lower than the mean cell size of the second emulsion.

12. The process of claim 11 wherein the first emulsion is prepared such that the mean cell size is at least about 35% lower than the mean cell size of the second emulsion.

13. The process of claim 3 wherein the monomer components in the oil phase of the first water-in-oil emulsion are completely polymerized prior to being combined with the second emulsion.

14. The process of claim 13 wherein the first emulsion comprises at least about 20% less than the second emulsion of the monofunctional monomer capable of forming an atactic amorphous polymer having a Tg of about 25° C. or lower.

15. The process of claim 13 wherein the first emulsion comprises at least about 20% more than the second emulsion of the first substantially water-insoluble, polyfunctional crosslinking agent.

16. The process of claim 13 wherein the first emulsion has a water-to-oil ratio that is at least about 20% more than the water-to-oil ratio of the second emulsion.

17. The process of claim 13 wherein the first emulsion is prepared such that the mean cell size is at least about 20% greater than the mean cell size of the second emulsion.

18. The process of claim 4 wherein the process conditions are varied rhythmically using a single emulsion forming head, wherein the mixing rate is varied such that the emulsion's mean cell size changes by at least 20%.

19. A process for making a heterogeneous polymeric foam structure of interconnected open-cells, wherein the foam structure has at least two distinct regions that differ by at least about 20% with regard to one or more of polymer density, polymer composition, surface properties, or microcellular morphology, the process comprising the steps of:

A) forming a first water-in-oil emulsion from:
1) an oil phase comprising:
a) from about 85 to about 98% by weight of a monomer component capable of forming a copolymer having a Tg of about 95° C. or lower, the monomer component comprising:
i) from about 20 to about 70% by weight of at least one substantially water-insoluble monofunctional monomer capable of forming an atactic amorphous polymer having a Tg of about 25° C. or lower;
ii) from about 10 to about 50% by weight of at least one substantially water-insoluble monofunctional comonomer capable of imparting toughness about equivalent to that provided by styrene;
iii) from about 5 to about 50% by weight of a first substantially water-insoluble, polyfunctional crosslinking agent selected from divinylbenzenes, trivinylbenzenes, divinyltoluenes, divinylxylenes, divinylnaphthalenes, divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinylsulfone, and mixtures thereof; and
iv) from 0 to about 15% by weight of a second substantially water-insoluble, polyfunctional crosslinking agent selected from polyfunctional acrylates, methacrylates, acrylamides, methacrylamides, and mixtures thereof; and
b) from about 2 to about 15% by weight of an emulsifier component which is soluble in the oil phase and which is capable of forming a stable water-in-oil emulsion, the emulsifier component comprising a primary emulsifier having at least about 40% by weight emulsifying components selected from diglycerol monoesters of branched $C_{16}$–$C_{24}$ fatty acids, linear unsaturated $C_{16}$–$C_{22}$ fatty acids, and linear saturated $C_{12}$–$C_{14}$ fatty acids; sorbitan monoesters of branched $C_{16}$–$C_{24}$ fatty acids, linear unsaturated $C_{16}$–$C_{22}$ fatty acids, linear saturated $C_{12}$–$C_{14}$ fatty acids; diglycerol monoaliphatic ethers of branched $C_{16}$–$C_{24}$ alcohols, linear unsaturated $C_{16}$–$C_{22}$ alcohols, and linear saturated $C_{12}$–$C_{14}$ alcohols, and mixtures thereof; and
2) a water phase comprising an aqueous solution containing: (a) from about 0.2 to about 20% by weight of a water-soluble electrolyte; and (b) an effective amount of a polymerization initiator;
3) a volume to weight ratio of water phase to oil phase in the range of from about 20:1 to about 200:1;

B) forming a second, distinct water-in-oil emulsion which is different in at least one respect from the first emulsion, but which comprises materials and ranges selected from those listed in parts A)1), A)2), and A)3); and C) (1) combining the first and second water-in-oil emulsions in a forming vessel prior to polymerizing the monomer components of either of the water-in-oil emulsions; and
(2) polymerizing both emulsions to form a polymeric, heterogenous foam.

20. The process of claim 19 wherein the first emulsion comprises at least about 20% more than the second emulsion of the monofunctional monomer capable of forming an atactic amorphous polymer having a Tg of about 25° C. or lower.

21. The process of claim 19 wherein the first emulsion comprises at least about 20% more than the second emulsion of the first substantially water-insoluble, polyfunctional crosslinking agent.

* * * * *

UNITED STATES PATENT AND TRADEMARK OFFICE
CERTIFICATE OF CORRECTION

PATENT NO. : 5,856,366
DATED : January 5, 1999
INVENTOR(S) : Thomas Michael Shiveley et al.

It is certified that error appears in the above-identified patent and that said Letters Patent is hereby corrected as shown below:

Column 19,
Line 12, "divinyifurans" should read -- divinylfurans --.

Column 37,
Line 3, "competition" should read -- composition --.
Line 26, "divinyiphenanthrenes" should read -- divinylphenanthrenes --.

Signed and Sealed this

Twenty-sixth Day of March, 2002

Attest:

JAMES E. ROGAN
Attesting Officer                Director of the United States Patent and Trademark Office